US009810165B2

(12) United States Patent
Ikemoto et al.

(10) Patent No.: US 9,810,165 B2
(45) Date of Patent: Nov. 7, 2017

(54) INTERNAL COMBUSTION ENGINE

(71) Applicant: TOYOTA JIDOSHA KABUSHIKI KAISHA, Toyota-shi, Aichi-ken (JP)

(72) Inventors: Masato Ikemoto, Susono (JP); Masayoshi Nakagawa, Mishima (JP); Takashi Matsumoto, Gotenba (JP); Yoshio Yamashita, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 14/761,706

(22) PCT Filed: Jan. 15, 2014

(86) PCT No.: PCT/JP2014/050604
§ 371 (c)(1),
(2) Date: Jul. 17, 2015

(87) PCT Pub. No.: WO2014/112538
PCT Pub. Date: Jul. 24, 2014

(65) Prior Publication Data
US 2015/0354475 A1 Dec. 10, 2015

(30) Foreign Application Priority Data
Jan. 21, 2013 (JP) .................................. 2013-008208

(51) Int. Cl.
*F02D 35/02* (2006.01)
*F02D 35/00* (2006.01)
(Continued)

(52) U.S. Cl.
CPC .............. *F02D 35/025* (2013.01); *F01P 7/14* (2013.01); *F02D 35/0007* (2013.01);
(Continued)

(58) Field of Classification Search
CPC .. Y02T 10/123; F02M 2200/05; F02M 53/04; F02M 61/18; F02M 43/04; F02M 31/18; F02M 57/00; F02M 61/16; F02M 69/045
(Continued)

(56) References Cited

U.S. PATENT DOCUMENTS 2,245,839 A * 6/1941 Tinker .................... F04F 5/461
417/166
5,271,358 A * 12/1993 Katoh .................... F02B 33/04
123/533

(Continued)

FOREIGN PATENT DOCUMENTS

DE    10 2010 016 554 A1    10/2010
JP          06147063 A *    5/1994
(Continued)

OTHER PUBLICATIONS

Machine Translation of JP2012281488, published 2012, see "JP2012281488_MachineTranslation.pdf".*

Primary Examiner — Long T Tran
(74) Attorney, Agent, or Firm — Finnegan, Henderson, Farabow, Garrett & Dunner, LLP

(57) ABSTRACT

An internal combustion engine includes a control unit determining the occurrence or non-occurrence of dew condensation in a tip portion of a nozzle based on a nozzle heat receiving amount of an injector and a nozzle tip temperature of the injector at a point in time when ignition is turned OFF and performing nozzle corrosion prevention control when the dew condensation is determined to occur in the nozzle tip portion. The control unit calculates a nozzle tip temperature reduction rate based on the nozzle heat receiving amount, calculates a dew point arrival time based on the reduction rate, and determines the occurrence or non-occurrence of the dew condensation in the nozzle tip portion based on the dew point arrival time.

9 Claims, 19 Drawing Sheets

(51) Int. Cl.
  *F01P 7/14*     (2006.01)
  *G01N 25/66*    (2006.01)
  *F02M 53/04*    (2006.01)
  *F02D 41/04*    (2006.01)

(52) U.S. Cl.
  CPC ............ *F02M 53/04* (2013.01); *G01N 25/66* (2013.01); *F02D 41/042* (2013.01); *F02M 2200/05* (2013.01)

(58) Field of Classification Search
  USPC ..... 123/142.5 R, 305, 298, 406.47, 467, 470
  See application file for complete search history.

(56) References Cited

U.S. PATENT DOCUMENTS

| | | | | |
|---|---|---|---|---|
| 5,839,890 | A * | 11/1998 | Snyder | F23D 14/48 |
| | | | | 239/553 |
| 6,922,987 | B2 * | 8/2005 | Mital | F01N 3/0871 |
| | | | | 60/286 |
| 7,343,895 | B2 * | 3/2008 | Mark | F02M 53/08 |
| | | | | 123/27 GE |
| 2015/0136100 | A1 | 5/2015 | Ikemoto | |

FOREIGN PATENT DOCUMENTS

| | | | |
|---|---|---|---|
| JP | H09-324704 A | | 12/1997 |
| JP | 10252578 A | * | 9/1998 |
| JP | 2010-255462 | | 11/2010 |
| JP | 2013189873 A | * | 9/2013 |
| JP | 2014125909 A | * | 7/2014 |

* cited by examiner

MANNER IN WHICH NOZZLE TIP TEMPERATURE IS
REDUCED AFTER ENGINE IS STOPPED

DEW CONDENSATION OCCURRENCE CONDITION

CHANGE IN NOZZLE TIP TEMPERATURE CAUSED BY RACING

CHANGE IN NOZZLE TIP TEMPERATURE CAUSED BY IDLE EXTENSION

EFFECT OF PISTON COOLING

EFFECT OF FIRST RADIATOR COOLANT INTRODUCTION

INTERNAL COMBUSTION ENGINE

CROSS-REFERENCE TO RELATED APPLICATIONS

This application is a national phase application of International Application No. PCT/JP2014/050604, filed Jan. 15, 2014, and claims the priority of Japanese Application No. 2013-008208, filed Jan. 21, 2013, the content of both of which is incorporated herein by reference.

TECHNICAL FIELD

The present invention relates to an internal combustion engine.

BACKGROUND ART

It has been known that an injection hole disposed in a nozzle tip portion of an injector injecting a fuel into a cylinder of an internal combustion engine may be subjected to corrosion because acid-containing moisture causes dew condensation in and condensed water adheres to the nozzle tip portion. Whether the dew condensation in the nozzle tip portion occurs or not is affected by the relationship between the temperature of the nozzle tip and the dew point of the in-cylinder atmosphere. In view of this point, PTL 1 proposes corrosion reduction by means of nozzle tip temperature estimation and EGR amount adjustment based on the estimated nozzle tip temperature.

CITATION LIST

Patent Literature

PTL 1: Japanese Patent Application Publication No. 2010-255462

SUMMARY OF THE INVENTION

The nozzle tip temperature is involved with the adherence of condensed water to the nozzle tip portion as disclosed in PTL 1. However, the nozzle tip temperature is continuously reduced after the engine is stopped. Accordingly, even if the nozzle tip temperature at a certain point in time is acquired, it is difficult to accurately predict the course of the nozzle tip temperature reduction following that point in time and reaching the occurrence of the dew condensation. Accordingly, PTL 1 has room for improvement regarding the determination of condensed water generation, that is, the occurrence of dew condensation.

An object of the internal combustion engine that is disclosed in this specification is to accurately determine the occurrence of dew condensation in a nozzle tip portion so as to effectively inhibit the dew condensation in the nozzle tip portion.

In order to solve the problem described above, an internal combustion engine that is disclosed in this specification includes a control unit determining the occurrence or non-occurrence of dew condensation in a tip portion of a nozzle based on a nozzle heat receiving amount of an injector and a nozzle tip temperature of the injector at a point in time when ignition is turned OFF. This control unit may perform at least one of control for nozzle heat dissipation rate reduction and control for the improvement of the temperature reduction rate of a part positioned around the nozzle when the dew condensation is determined to occur in the nozzle tip portion.

The nozzle tip temperature is involved in the occurrence of the dew condensation in and condensed water adherence to the nozzle tip portion. The change in the nozzle tip temperature that follows the stopping of the engine is affected by the nozzle heat receiving amount of the injector at the point in time when the ignition is turned OFF. Accordingly, the change in the nozzle tip temperature can be accurately grasped and the occurrence or non-occurrence of the dew condensation in the nozzle tip portion can be more accurately determined when the nozzle heat receiving amount is taken into account.

Even if the nozzle tip temperatures at the point in time when the ignition is turned OFF are equal to each other, the nozzle tip temperature reduction rate thereafter is more gradual and the length of time until a dew point is reached increases when the nozzle heat receiving amount until the point in time is reached is large. When the dew point arrival time of the nozzle tip temperature is increased, it becomes more likely that the temperature of another part around the nozzle reaches the dew point before the nozzle tip temperature reaches the dew point. When the temperature of the other part reaches the dew point before the nozzle tip temperature reaches the dew point, the dew condensation occurs in that part and the dew condensation in the nozzle tip portion is avoided.

The control unit performs at least one of the control for the nozzle heat dissipation rate reduction and the control for the improvement of the temperature reduction rate of the part positioned around the nozzle when the dew condensation is determined to occur in the nozzle tip portion. The heat dissipation rate of the nozzle tip portion is relatively reduced compared to a case where no measure is taken. In other words, control for maintaining the nozzle tip temperature to the maximum extent possible and for reducing the temperature of the part positioned around the nozzle to the maximum extent possible is performed. In other words, at least any one of a measure for the slowdown of the nozzle tip temperature reduction rate and a measure for the improvement of the temperature reduction rate of the part positioned around the nozzle may be taken.

The control unit may calculate the nozzle tip temperature reduction rate based on the nozzle heat receiving amount, may calculate the dew point arrival time based on the nozzle tip temperature reduction rate, and may determine the occurrence or non-occurrence of the dew condensation in the nozzle tip portion based on the dew point arrival time.

The control unit may perform racing implementation control during the control for the nozzle heat dissipation rate reduction. In addition, the control unit may perform idle extension control during the control for the nozzle heat dissipation rate reduction. In addition, the control unit may raise an idle rotation speed during the idle extension control.

The nozzle heat receiving amount can be increased when the racing implementation control, the idle extension control, or the measure for raising the idle rotation speed is performed. When the nozzle heat receiving amount is increased, the heat dissipation rate of the nozzle following the increase in the nozzle heat receiving amount becomes gradual and the nozzle tip temperature reduction rate is reduced. In other words, the nozzle tip temperature becomes less likely to be reduced. As a result, the dew point arrival time can be increased and the dew condensation in the nozzle tip portion can be inhibited.

The control unit may improve a piston temperature reduction rate during the control for the improvement of the temperature reduction rate of the part positioned around the nozzle. When a piston is selected as the part positioned around the nozzle and the piston temperature reduction rate is improved, the timing when the piston reaches the dew point temperature precedes the timing when the nozzle reaches the dew point temperature. Accordingly, the dew condensation in the nozzle tip portion is avoided.

The control unit may introduce a coolant in a radiator into an engine main body and may improve a cylinder bore wall temperature reduction rate during the control for the improvement of the temperature reduction rate of the part positioned around the nozzle. When a bore wall is selected as the part positioned around the nozzle and the bore wall temperature reduction rate is improved, the timing when the bore wall reaches the dew point temperature precedes the timing when the nozzle reaches the dew point temperature. Accordingly, the dew condensation in the nozzle tip portion is avoided.

The control unit may reduce, that is, slow down the nozzle tip temperature reduction rate by supplying hot water in a heat storage tank to a cylinder head on which the injector is mounted during the control for the improvement of the temperature reduction rate of the part positioned around the nozzle. Heat dissipation from the nozzle becomes less likely to occur when the heat amount of the cylinder head on which the injector is mounted rises. As a result, the nozzle tip temperature reduction rate becomes gradual. Then, the dew point arrival time of the nozzle tip portion is increased and the dew condensation in the nozzle tip portion becomes less likely to occur.

According to the internal combustion engine disclosed in the specification, the occurrence of the dew condensation in the nozzle tip portion can be accurately determined.

MODES FOR CARRYING OUT THE INVENTION

Figure 1:
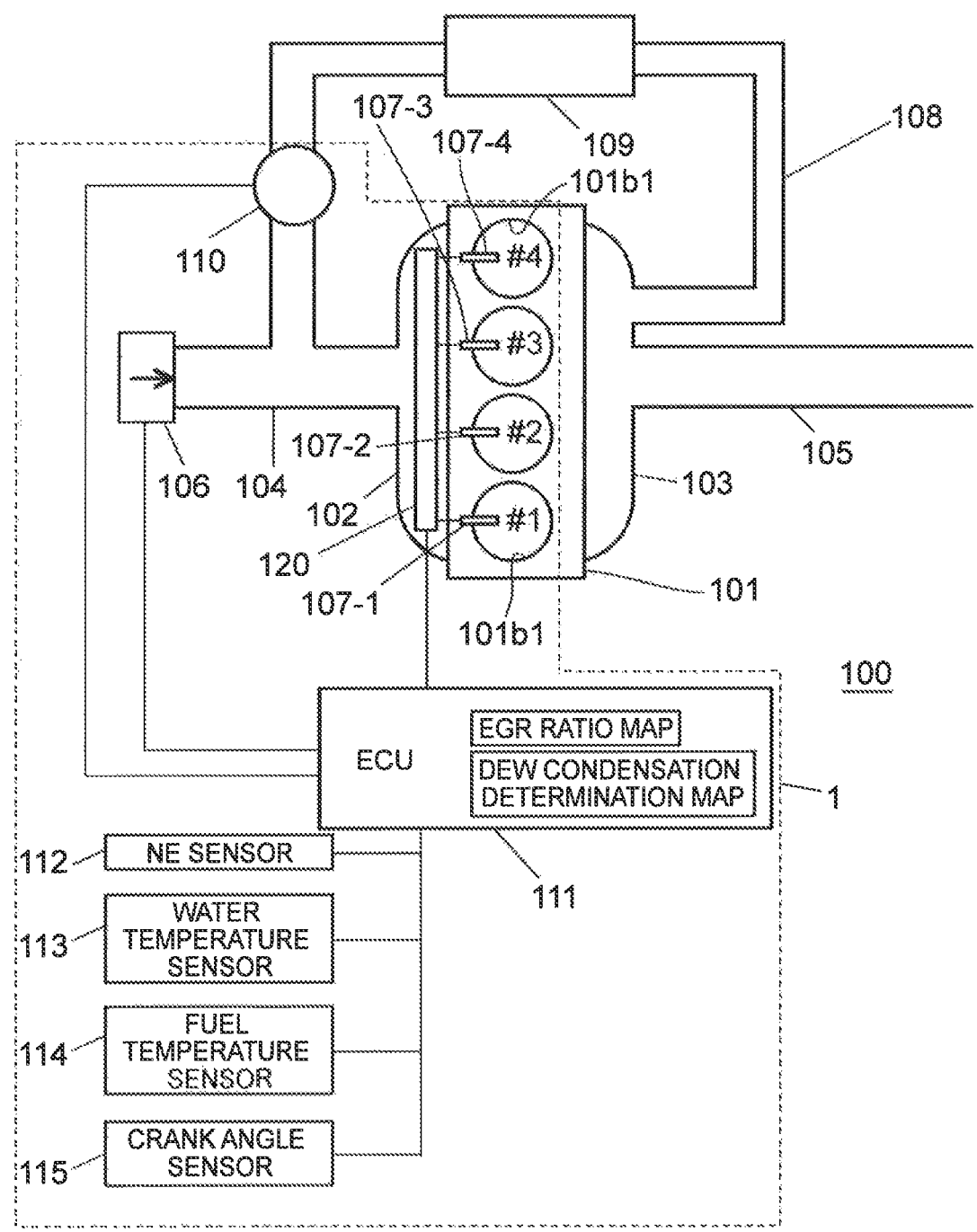
FIG. 1 is an explanatory drawing illustrating a schematic configuration of an internal combustion engine according to a first embodiment.

Hereinafter, embodiments of the invention will be described with reference to accompanying drawings. In some cases, the dimensions, ratios, and the like of the respective portions in the drawings may not exactly match the actual ones and some details may not be illustrated in the drawings.

First Embodiment

FIG. 1 is an explanatory drawing illustrating a schematic configuration of an internal combustion engine 100 according to a first embodiment. A fuel injection device 1 is incorporated into the internal combustion engine 100. The internal combustion engine 100 is an internal combustion engine that performs in-cylinder injection, more specifically, a diesel internal combustion engine. The internal combustion engine 100 is a four-cylinder internal combustion engine. The internal combustion engine 100 is provided with an engine main body 101 that is provided with a cylinder head 101a and a cylinder block 101b, and is provided with #1 to #4 cylinders in the engine main body 101. The fuel injection device 1 is incorporated into the internal combustion engine 100. The fuel injection device 1 is provided with #1 to #4 injectors 107-1 to 107-4 corresponding to the #1 to #4 cylinders. Specifically, the #1 injector 107-1 is mounted on the #1 cylinder, the #2 injector 107-2 is mounted on the #2 cylinder, the #3 injector 107-3 is mounted on the #3 cylinder, and the #4 infector 107-4 is mounted on the 44 cylinder. Each of the #1 to #4 injectors 107-1 to 107-4 is connected to a common rail 120, and a high-pressure fuel is supplied from the common rail 120. Each of the injectors 107 is mounted on the cylinder head 101a. Each of the injectors 107 exchanges heat with the cylinder head 101a via a seat portion.

The internal combustion engine 100 is provided with an intake manifold 102 and an exhaust manifold 103 mounted on the engine main body 101. An intake pipe 104 is connected to the intake manifold 102. An exhaust pipe 105 is connected to the exhaust manifold 103 and one end of an EGR passage 108 is connected to the exhaust manifold 103. The other end of the EGR passage 108 is connected to the intake pipe 104. An EGR cooler 109 is disposed in the EGR passage 108. An EGR valve 110 that controls an exhaust gas flow state is disposed in the EGR passage 108. An air flow meter 106 is connected to the intake pipe 104. The air flow meter 106 is electrically connected to an ECU 111. The injectors 107-$i$ (i representing a cylinder number), specifically, #1 to #4 injectors 107-1 to 107-4, are electrically connected to the ECU 111. The ECU 111, which corresponds to a control unit, performs various types of control described later.

An NE sensor 112 that measures the rotation speed of the internal combustion engine, a water temperature sensor 113 that measures the temperature of a coolant, a fuel temperature sensor 114 that measures the temperature of the fuel, and a crank angle sensor 115 are electrically connected to the ECU 111. In addition, an EGR ratio map, a dew condensation determination map, and other maps are stored in the ECU 111. The ECU 111 controls various types of control around the internal combustion engine.

Figure 2:
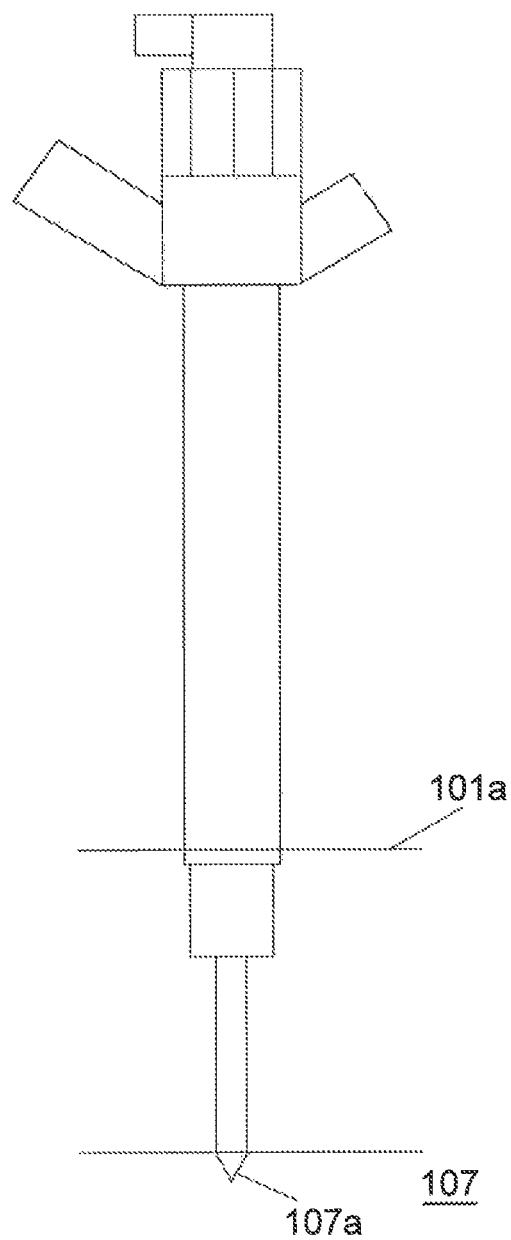
FIG. 2 is an explanatory drawing of an injector that is mounted on the internal combustion engine.

Referring to FIG. 2 illustrating the injector 107 that is mounted on the internal combustion engine 100, the injector 107 is provided with a nozzle 107$a$ in a tip portion. An injection hole is disposed in the nozzle 107$a$. Corrosion may occur when condensed water containing an acid component causes dew condensation in and adheres to the tip portion of the nozzle 107$a$. When the corrosion occurs around the injection hole, the diameter of the injection hole may change. Appropriate fuel injection is affected when the diameter of the injection hole changes. The ECU 111 determines the occurrence or nonoccurrence of the dew condensation and performs nozzle corrosion prevention control. The injector 107 is mounted on the cylinder head 101$a$.

Figure 3:
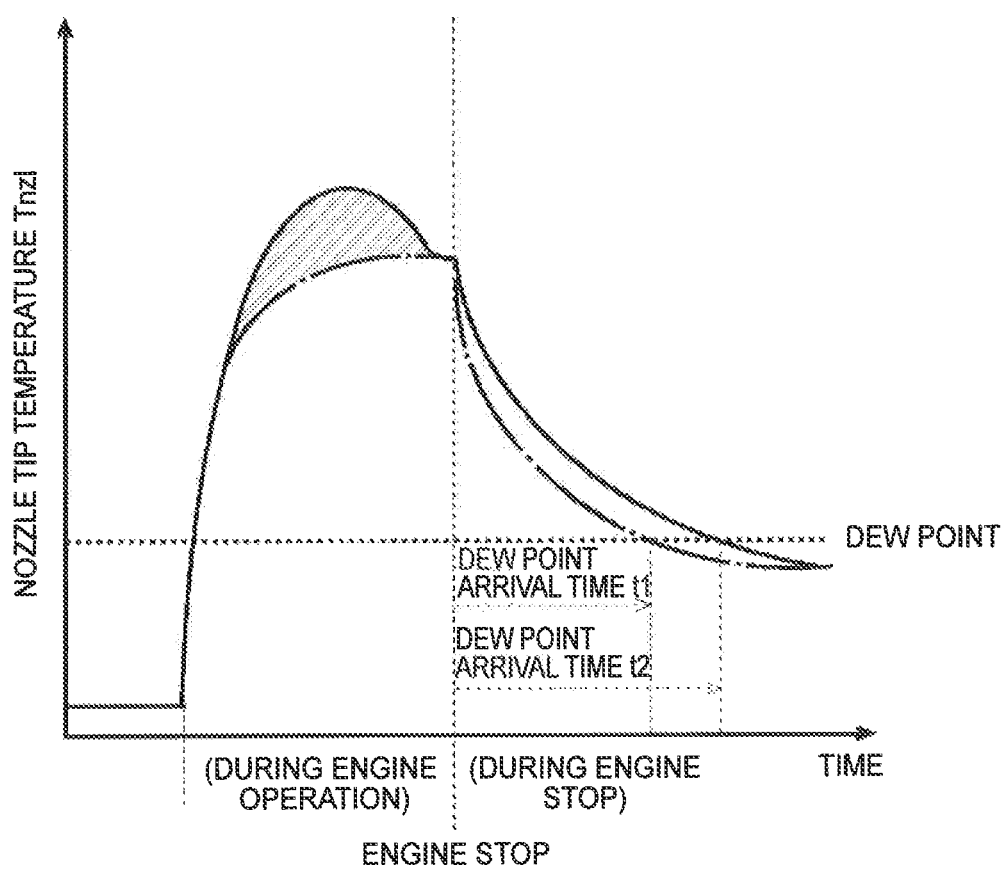
FIG. 3 is an explanatory drawing illustrating how a nozzle tip temperature is reduced after the internal combustion engine is stopped.

Hereinafter, how the temperature of the nozzle tip is reduced after the engine is stopped will be described with reference to FIG. 3. Both the solid line and the one-dot chain line in FIG. 3 show the transition of the nozzle tip temperature preceding and following the stopping of the engine. The nozzle tip temperature in the solid line and the nozzle tip temperature in the one-dot chain line are equal to each other when the engine is stopped. The rate at which the nozzle tip temperature is reduced in the solid line is more gradual and slower than the rate at which the nozzle tip temperature is reduced in the one-dot chain line after the engine is stopped. As a result, the length of time t2 for the nozzle tip temperature shown by the solid line to reach a dew point exceeds the length of time t1 for the nozzle tip temperature shown by the one-dot chain line to reach the dew point. When the dew point arrival time is longer, dew condensation is more likely to occur at a part other than the nozzle tip portion, and a longer dew point arrival time is more advantageous in terms of nozzle corrosion prevention. The nozzle tip temperature reduction rates are different from each other as described above, despite the nozzle tip temperatures being equal to each other when the engine is stopped, because nozzle heat receiving amounts prior to the stopping of the engine are different from each other. The nozzle heat receiving amounts can include heat receiving amounts around the nozzles. In other words, the nozzle heat receiving amounts can include the heat receiving amount of the cylinder head 101$a$ on which the injectors 107 are mounted. Referring to FIG. 3, the solid line and the one-dot chain line have different nozzle tip temperature histories. As a result, the nozzle heat receiving amount is greater, by a margin of the hatching part illustrated in FIG. 3, in the solid line than in the one-dot chain line. It is conceivable that this difference between the nozzle heat receiving amounts is shown as the difference between the nozzle tip temperature reduction rates following the stopping of the engine.

Figure 4:
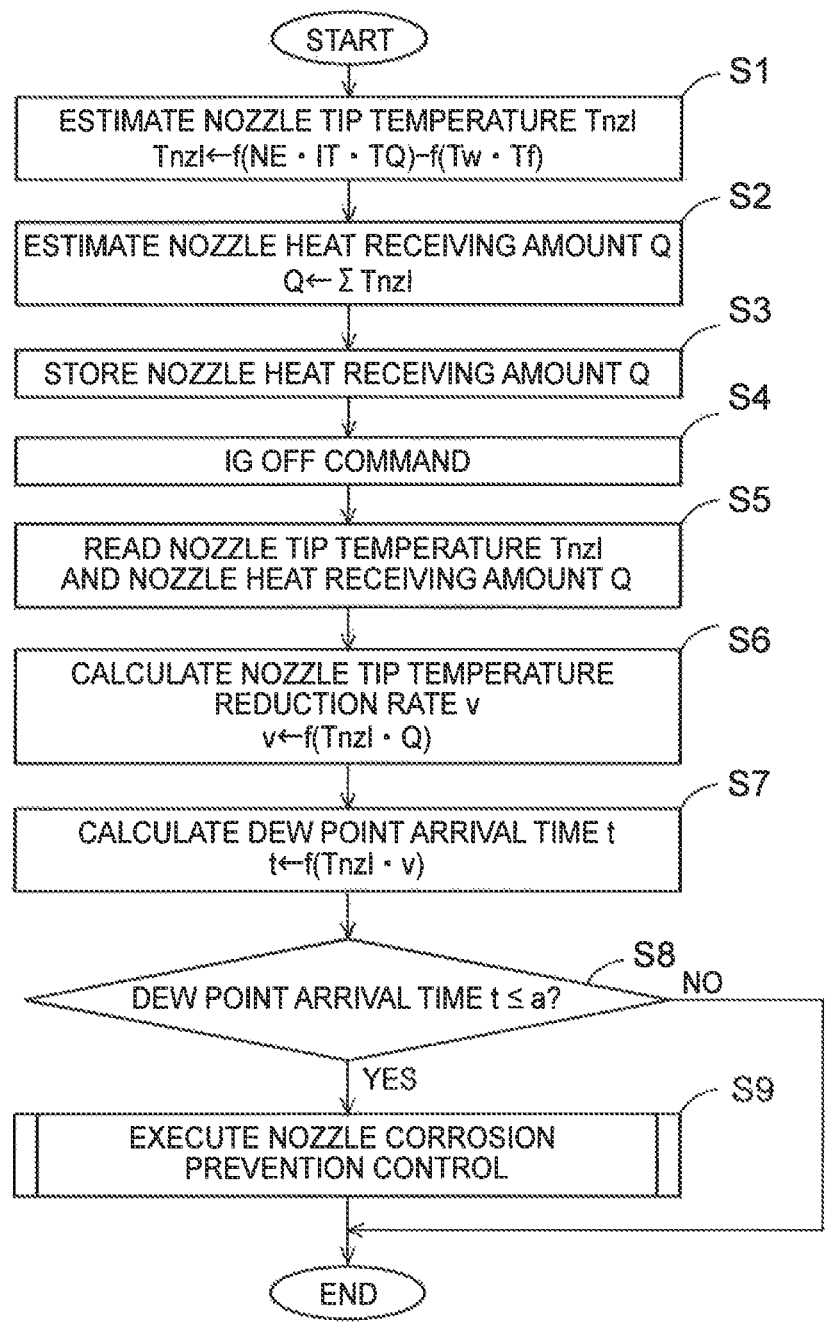
FIG. 4 is a how diagram illustrating an example of the control of the internal combustion engine according to the first embodiment.
Figure 5:
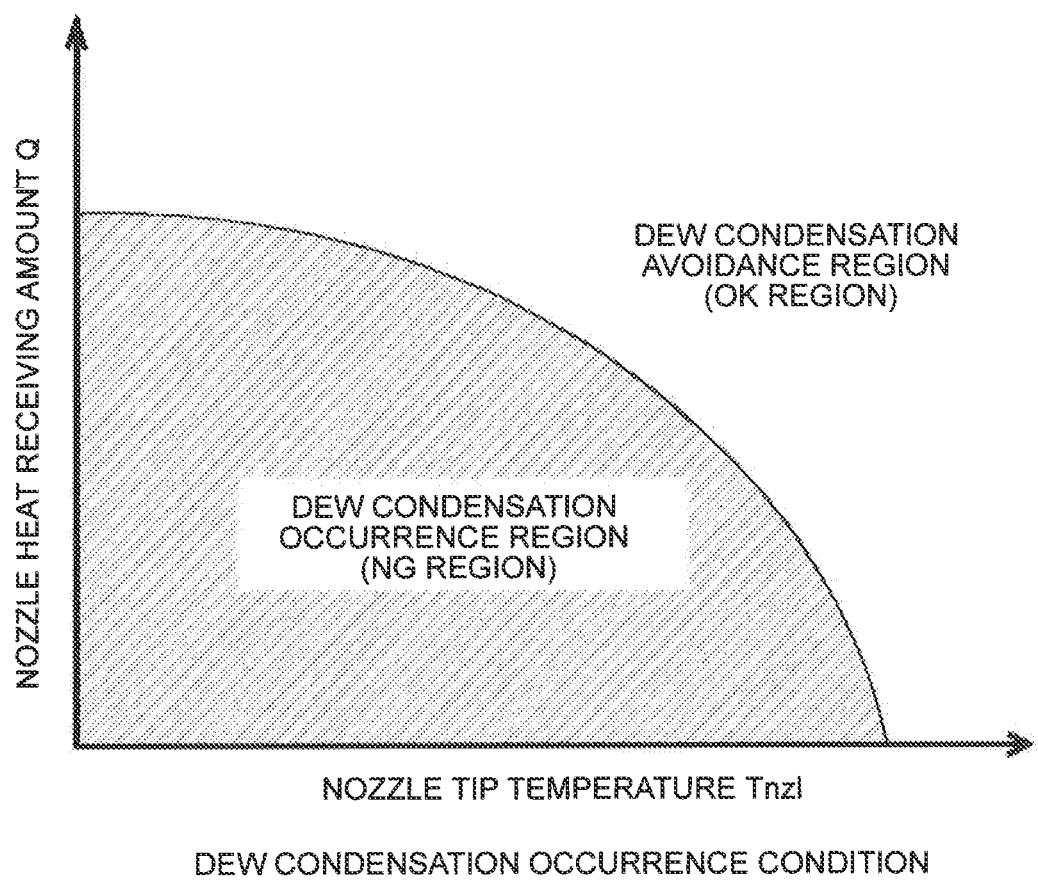
FIG. 5 is an example of a map illustrating a dew condensation occurrence condition.
Figure 6:
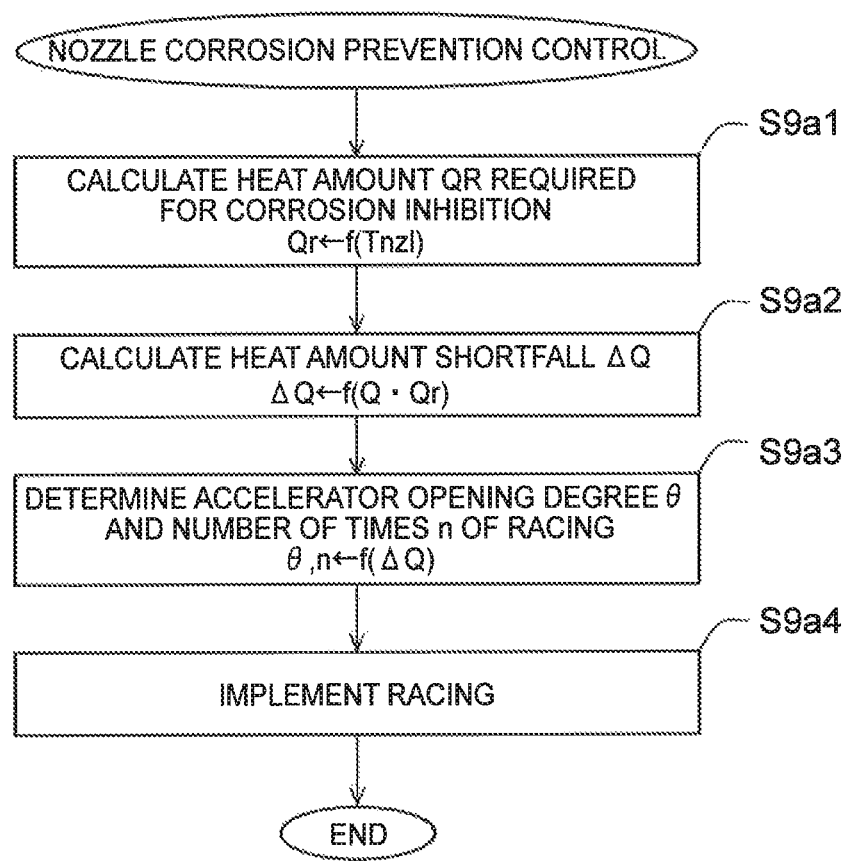
FIG. 6 is a flow diagram illustrating an example of nozzle corrosion prevention control according to the first embodiment.
Figure 7:
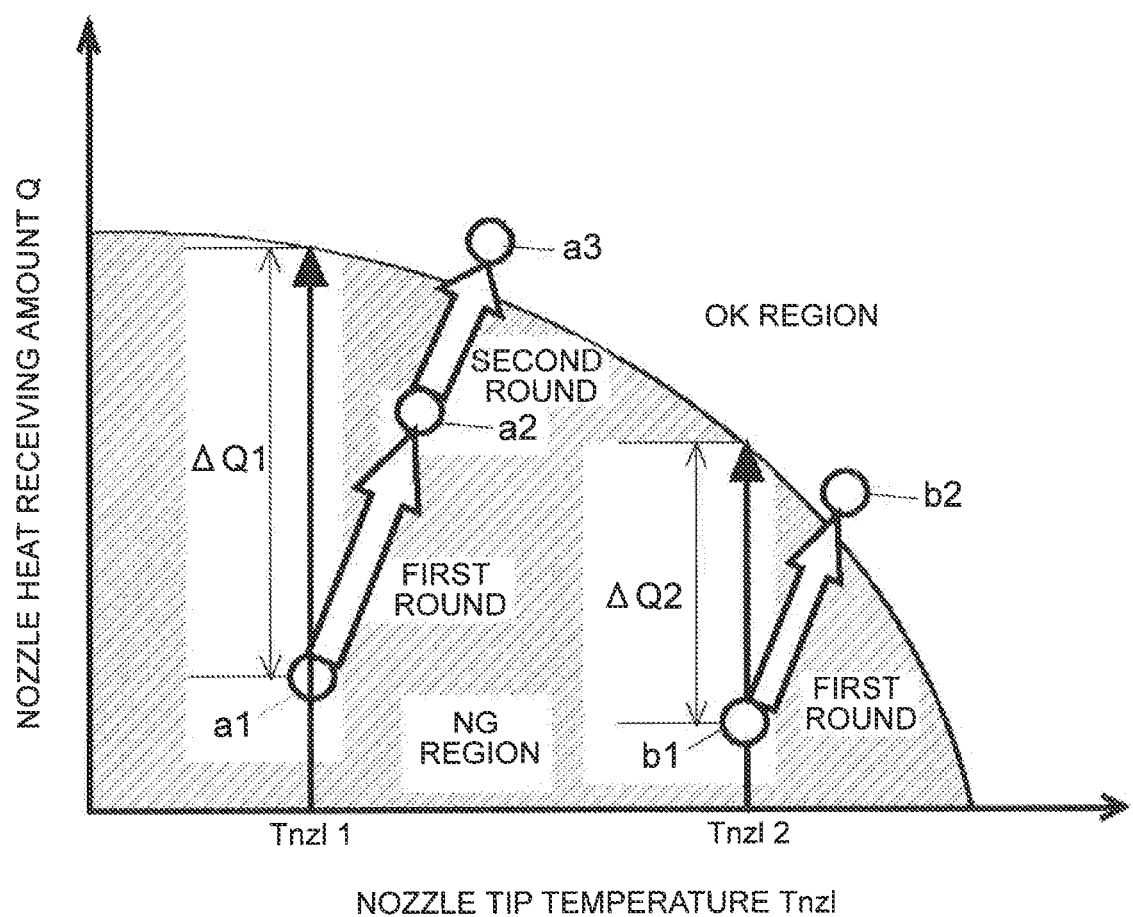
FIG. 7 is an explanatory drawing illustrating how the nozzle tip temperature is changed by racing.

In the internal combustion engine 100 according to this embodiment, the occurrence or non-occurrence of the dew condensation in the nozzle tip portion is determined based on the nozzle heat receiving amount. Hereinafter, an example of the control of the internal combustion engine 100 will be described with reference to FIGS. 4 to 7. FIG. 4 is a flow diagram illustrating an example of the control of the internal combustion engine 100. FIG. 5 is an example of a map illustrating a dew condensation occurrence condition. FIG. 6 is a flow diagram illustrating an example of the nozzle corrosion prevention control for the internal combustion engine 100. FIG. 7 is an explanatory drawing illustrating how the nozzle tip temperature is changed by racing implemented as the nozzle corrosion prevention control. The ECU 111, which functions as the control unit, leads the control of the internal combustion engine 100.

Firstly, an arithmetic operation for the estimation of the nozzle tip temperature Tnzl is performed in Step S1. The nozzle tip temperature Tnzl is a nozzle tip temperature by point in time, that is, a momentary nozzle tip temperature. The nozzle tip temperature Tnzl is calculated and estimated by using, for example, the following Equation 1.

$$Tnzl = f(NE \cdot IT \cdot TQ) - f(Tw \cdot Tf) \quad \text{Equation 1}$$

NE: engine rotation speed IT: injection timing TQ: injection amount

Tw: water temperature Tf: fuel temperature

Then, an arithmetic operation for the estimation of the nozzle heat receiving amount Q is performed in Step S2. The nozzle heat receiving amount Q can be obtained as a value in which the momentary nozzle tip temperature Tnzl calculated in Step S1 is integrated for a certain period of time τ. The nozzle heat receiving amount Q is calculated and estimated by using, for example, the following Equation 2. The certain period of time t is any period that can be set from an appropriate condition.

$$Q = \Sigma Tnzl \quad \text{Equation 2}$$

In Step S3 that follows Step S2, the nozzle heat receiving amount Q calculated in Step S2 is stored in the ECU 111. In Step S4 that follows Step S3, an ignition OFF (IG OFF) command is confirmed, and then the processing proceeds to Step S5. In Step S5, the nozzle tip temperature Tnzl and the nozzle heat receiving amount Q are read. The nozzle tip temperature Tnzl that is read herein is a value at the point in time when the ignition is turned OFF. The point in time when the ignition is turned OFF not only refers to a certain single point in time in a strict sense but also can be a point in time within the periods preceding and following the timing when the ignition is turned OFF. For example, the point in time when the ignition is turned OFF can be the point in time when the internal combustion engine 100 is stopped by the ignition being turned OFF.

In Step S6, the nozzle tip temperature reduction rate v is calculated based on the nozzle tip temperature Tnzl and the nozzle heat receiving amount Q read in Step S5. The reduction rate v is calculated by using, for example, the following Equation 3.

$$v = f(Tnzl \cdot Q) \quad \text{Equation 3}$$

In Step S7 that follows Step S6, the dew point arrival time t is calculated based on the nozzle tip temperature Tnzl read in Step S5 and the reduction rate v calculated in Step S6. The dew point arrival time t is calculated by using, for example, the following Equation 4.

$$t=f(Tnzl-v) \quad \text{Equation 4}$$

In Step S8 that follows Step S7, it is determined whether or not the dew point arrival time t is equal to or less than a threshold a determined in advance. The threshold a is a value that is determined by appropriateness by actual equipment as a value for the determination of whether or not the dew condensation occurs in the nozzle tip portion. In a case where the dew point arrival time t is exceeds the threshold a, it is determined that the occurrence of the dew condensation in the nozzle tip portion is avoided.

In the event of a No determination in Step S8, the processing is terminated. In other words, no particular nozzle corrosion prevention measure is required when the dew point arrival time t exceeds the threshold a because it is considered that the dew condensation occurs at a location other than the nozzle tip portion and the dew condensation in the nozzle tip portion is avoided in this case. In the event of a Yes determination in Step S8, the processing proceeds to Step S9, and the nozzle corrosion prevention control is performed. The nozzle corrosion prevention control is a subroutine, which will be described in detail later.

Since the nozzle heat receiving amount Q is taken into account as described above, the occurrence or non-occurrence of the dew condensation in the nozzle tip portion can be appropriately determined. As a result, it is possible to avoid a situation in which a necessary nozzle corrosion prevention measure is not taken and a situation in which a nozzle corrosion prevention measure is unnecessarily taken.

FIG. 5 is an example of a map illustrating the dew condensation occurrence condition. In view of the nozzle heat receiving amount Q described above, the dew condensation may occur in the nozzle tip portion even when the nozzle tip temperature Tnzl at a point in time, for example, the point in time when the ignition is turned OFF, is high. In contrast, the dew condensation in the nozzle tip portion may be avoided, even if the nozzle tip temperature Tnzl at the point in time when the ignition is turned OFF is low, when the nozzle heat receiving amount Q is large. The necessity of the execution of the nozzle corrosion prevention control may be determined by using the distinction between the dew condensation occurrence region and the dew condensation avoidance region based on the map illustrated in FIG. 5.

Hereinafter, specific details of the nozzle corrosion prevention control will be described with reference to FIGS. 6 and 7. As described above, FIG. 6 is a flow diagram illustrating an example of the nozzle corrosion prevention control (control for nozzle heat dissipation rate reduction) for the internal combustion engine 100. Specifically, FIG. 6 shows an example of racing implementation control.

In Step S9a1, a heat amount Qr that is required for corrosion inhibition is calculated. The heat amount Qr is calculated by using, for example, the following Equation 5.

$$Qr=f(Tnzl) \quad \text{Equation 5}$$

Herein, the value that is read in Step S5 of the flow diagram illustrated in FIG. 4 is used as the Tnzl. The heat amount Qr can be obtained as a heat amount for the nozzle tip temperature Tnzl to be fitted into the map illustrated in FIG. 5 and enter the dew condensation avoidance region (OK region).

In Step S9a2, a heat amount shortfall ΔQ is calculated. The ΔQ is calculated by using, for example, the following Equation 6.

$$\Delta Q=f(Q\cdot Qr) \quad \text{Equation 6}$$

Herein, the value that is read in Step S5 of the flow diagram illustrated in FIG. 4 used as the Q.

In Step S9a3, an arithmetic operation for the determination of an accelerator opening degree θ and the number of times n of the racing is performed. Then, in Step S9a4, no-load racing is actually performed. The change in the nozzle tip temperature Tnzl that is caused by the racing will be described with reference to FIG. 7. In a case where the nozzle tip temperature Tnzl is Tnzl1 in the state shown as the a1 in FIG. 7, for example, the heat amount is ΔQ1 short of a movement into the dew condensation avoidance region (OK region) out of the dew condensation occurrence region (NG region). When the heat amount of the case of a single racing at the determined accelerator opening degree θ is dQ, the number of times n of the racing is ΔQ÷dQ. When the number of times n of the racing that is calculated is 1.5, for example, the first round of the racing is performed at 100% of the opening degree θ. Then, the state shown as the a2 in FIG. 7 is achieved. The second round of the racing is performed at, for example, 70% of the opening degree θ to exceed 0.5 rounds. Then, the state shown as the a3 in FIG. 7 is achieved, and getting out to the OK region becomes possible.

In a case where the nozzle tip temperature Tnzl is Tnzl2 in the state shown as the b1 in FIG. 7, for example, the heat amount is ΔQ2 short of a movement into the dew condensation avoidance region (OK region) out of the dew condensation occurrence region (NG region). When the heat amount of the case of a single racing at the determined accelerator opening degree θ is dQ, the number of times n of the racing is ΔQ÷dQ. When the number of times n of the racing that is calculated is 0.8, for example, the first round of the racing is performed at 80% or more of the opening degree θ. Then, the state shown as the b2 in FIG. 7 is achieved, and getting out to the OK region becomes possible.

The amount of rise of the nozzle heat receiving amount Q per time can be increased when the accelerator opening degree θ is increased. However, an appropriate accelerator opening degree θ is used in view of noise or the like.

As described above, the nozzle heat receiving amount Q can be increased when the racing implementation control is performed. As a result, the nozzle heat dissipation rate of the injector can be reduced. When the nozzle heat dissipation rate is reduced, the reduction rate v of the nozzle tip temperature Tnzl is reduced, and the dew point arrival time t of the nozzle tip portion increases. In this manner, the occurrence of the dew condensation in the nozzle tip portion can be avoided.

Second Embodiment

Figure 8:
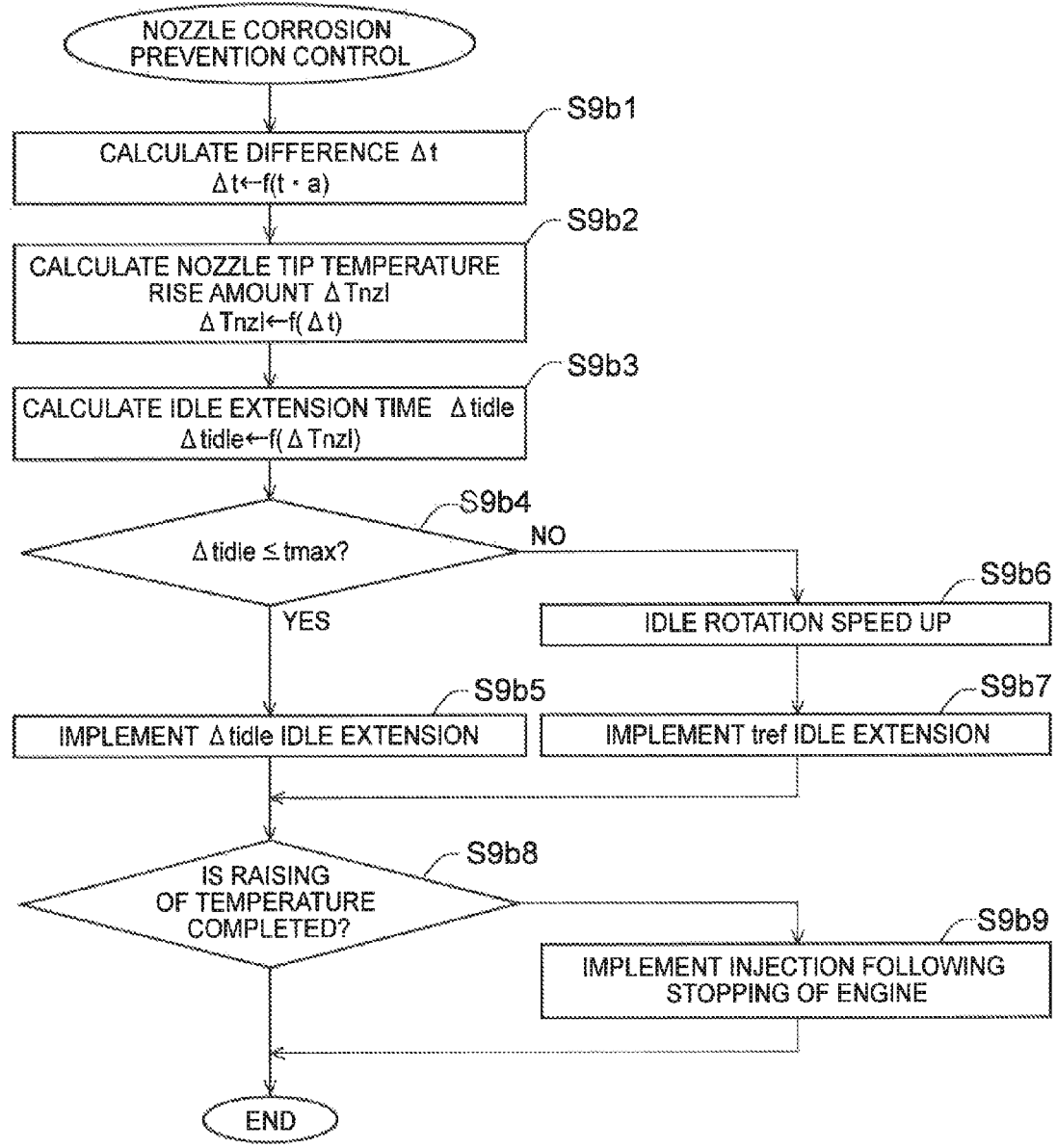
FIG. 8 is a flow diagram illustrating an example of nozzle corrosion prevention control according to a second embodiment.
Figure 9A:
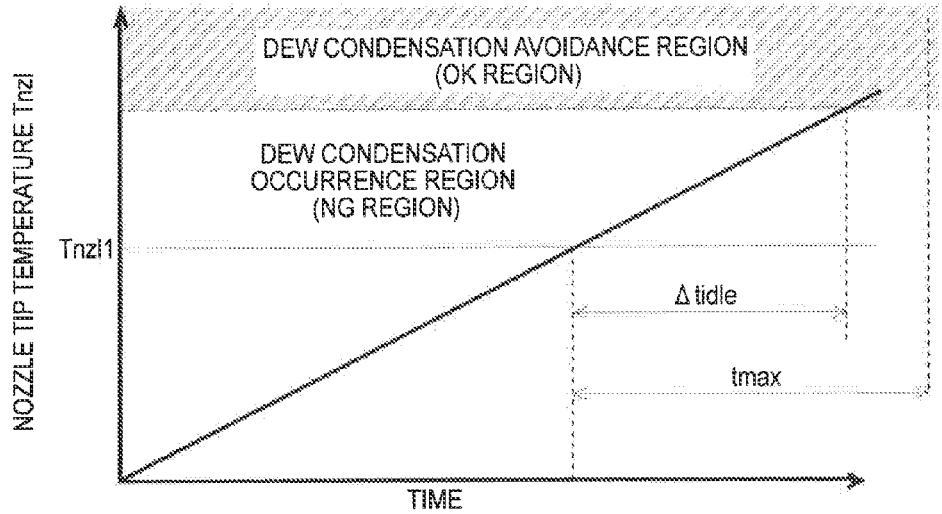
FIGS. 9A and 9B are graphs illustrating the change in the nozzle tip temperature that is caused by idle extension.
Figure 9B:
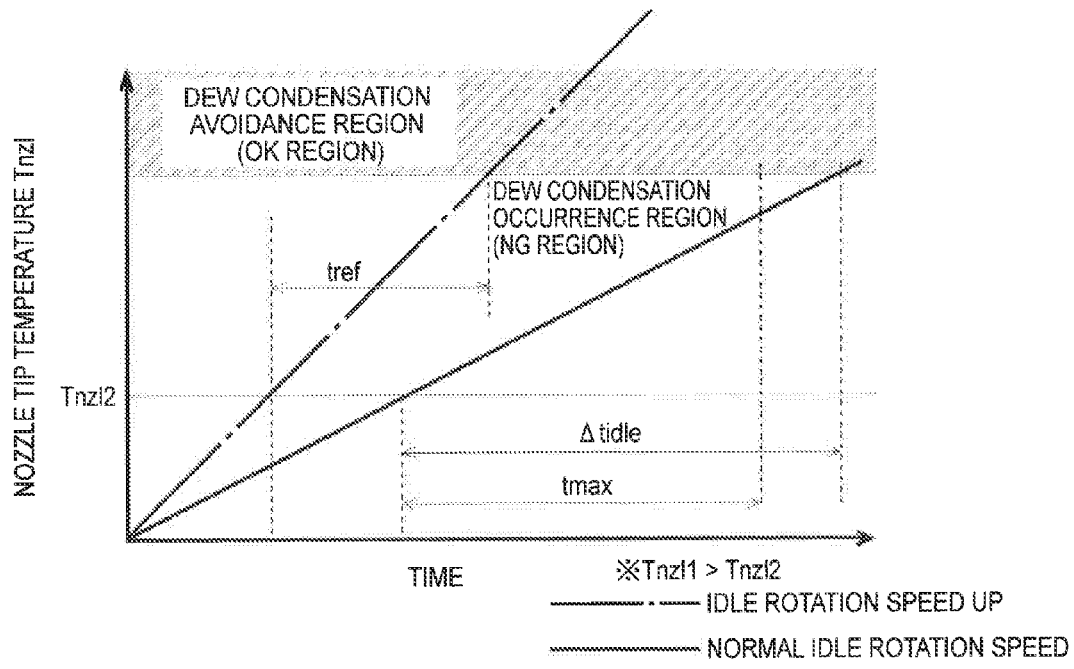

Hereinafter, a second embodiment will be described with reference to FIGS. 8 and 9. FIG. 8 is a flow diagram illustrating an example of the control of the internal combustion engine 100 according to the second embodiment, specifically, idle extension control. FIGS. 9A and 9B are graphs illustrating the change in the nozzle tip temperature that is caused by idle extension.

The difference between the second embodiment and the first embodiment lies in details of the nozzle corrosion prevention control (control for nozzle heat dissipation rate reduction) performed by the ECU 111. In the second embodiment, the idle extension control is performed instead of the racing implementation control of the first embodiment. In other words, the details of Steps S1 to S8 in the flow diagram illustrated in FIG. 4 are identical to those of the first embodiment. The basic configuration of the internal combustion engine 100 is identical to that of the first embodiment, and thus detailed description thereof will be omitted.

In Step S9b1, the ECU 111 calculates the difference Δt between the dew point arrival time t and the threshold a. The Δt is calculated by using the following Equation 7.

$$\Delta t = f(t \cdot a) \quad \text{Equation 7}$$

In the following Step S9b2, a nozzle tip temperature rise amount ΔTnzl is calculated. The nozzle tip temperature rise amount is calculated based on the difference Δt. The nozzle tip temperature rise amount is calculated by using, for example, the following Equation 8.

$$\Delta Tnzl = f(\Delta t) \quad \text{Equation 8}$$

In Step S9b3, an idle extension time Δtidle is calculated based on the nozzle tip temperature rise amount. The idle extension time Δtidle is calculated by using, for example, the following Equation 9.

$$\Delta tidle = f(\Delta Tnzl) \quad \text{Equation 9}$$

In Step S9b4, it is determined whether or not the Δtidle calculated in Step S9b3 is equal to or less than a threshold tmax determined in advance. The threshold tmax is a value that is defined as the maximum length of time allowed as the idle extension time. The threshold tmax can be determined in view of noise or the like.

In the event of a Yes determination in Step S9b4, the processing proceeds to Step S9b5, and the idle extension of the time Δtidle is implemented. An idle extension measure is implemented after it is confirmed that a vehicle gear is at neutral (N) or parking (P) and the side brake is applied.

In the event of a No determination in Step S9b4, the processing proceeds to Step S9b6. In Step S9b6, an idle rotation speed is raised. Then, in Step S9b7, the idle extension of a time tref allowing for the raised idle rotation speed is implemented.

After the implementation of the idle extension in Step S9b5 and Step S9b7, it is determined in Step S9b8 whether or not a required rise in temperature is completed. The processing is terminated (ends) in the event of a Yes determination in Step S9b8. In the event of a No determination in Step S9b8, the processing proceeds to Step S9b9, and injection following the stopping of the engine is implemented. In a case where it is impossible to avoid the dew condensation in the nozzle tip portion despite the raising of the idle rotation speed, an excessive idle extension is avoided and the fuel is allowed to adhere to the nozzle tip portion as the nozzle corrosion prevention measure. The processing is terminated (ends) after Step S9b9.

The change in the nozzle tip temperature that is caused by the idle extension will be described with reference to FIGS. 9A and 9B. FIG. 9A shows the change in the nozzle tip temperature caused by the idle extension pertaining to a case where the nozzle tip temperature Tnzl at the point in time when the ignition is turned OFF is Tnzl1. FIG. 9B shows the change in the nozzle tip temperature caused by the idle extension pertaining to a case where the nozzle tip temperature Tnzl at the point in time when the ignition is turned OFF is Tnzl2. Herein, the Tnzl1 exceeds the Tnzl2. Referring to FIG. 9A, the Δtidle is within the threshold tmax even at a normal idle rotation speed. Accordingly, it is possible for the nozzle tip temperature Tnzl to get out to the dew condensation avoidance region (OK region) when the idle extension of the Δtidle is implemented. Referring to FIG. 9B, the Δtidle exceeds the threshold tmax at a normal idle rotation speed. Herein, the idle rotation speed is raised. Then, the nozzle tip temperature Tnzl can get out to the dew condensation avoidance region (OK region) when the idle extension of the time tref is implemented.

As described above, the nozzle heat receiving amount Q can be increased when the idle extension control is performed. As a result, the nozzle heat dissipation rate of the injector can be reduced. When the nozzle heat dissipation rate is reduced, the reduction rate v of the nozzle tip temperature Tnzl is reduced, and the dew point arrival time t of the nozzle tip portion increases. In this manner, the occurrence of the dew condensation in the nozzle tip portion can be avoided.

Third Embodiment

Figure 10:
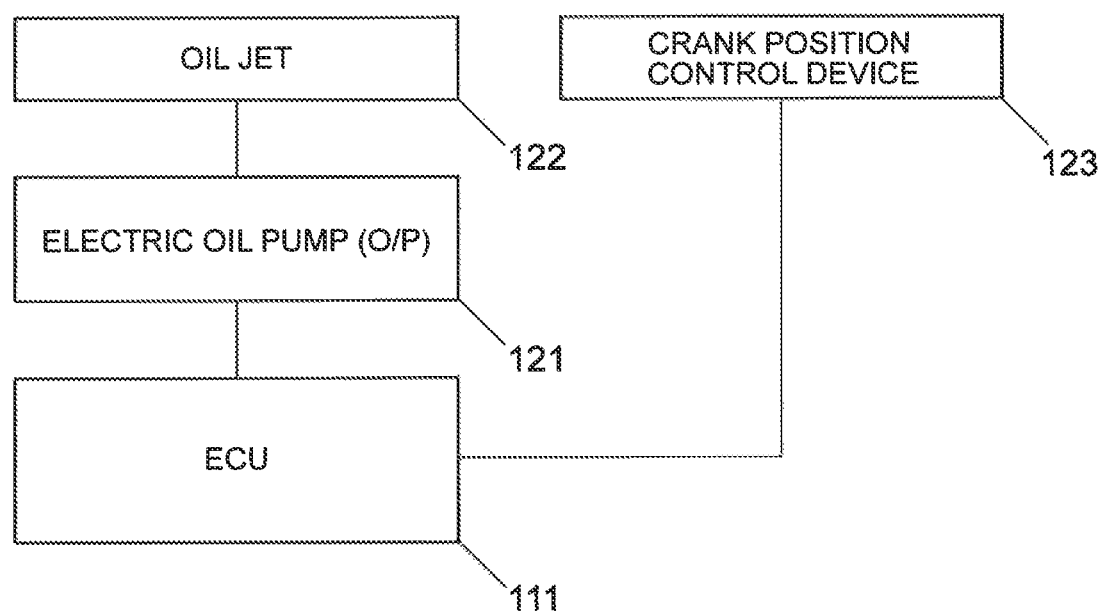
FIG. 10 is a block diagram illustrating a main part of an internal combustion engine according to a third embodiment.
Figure 11:
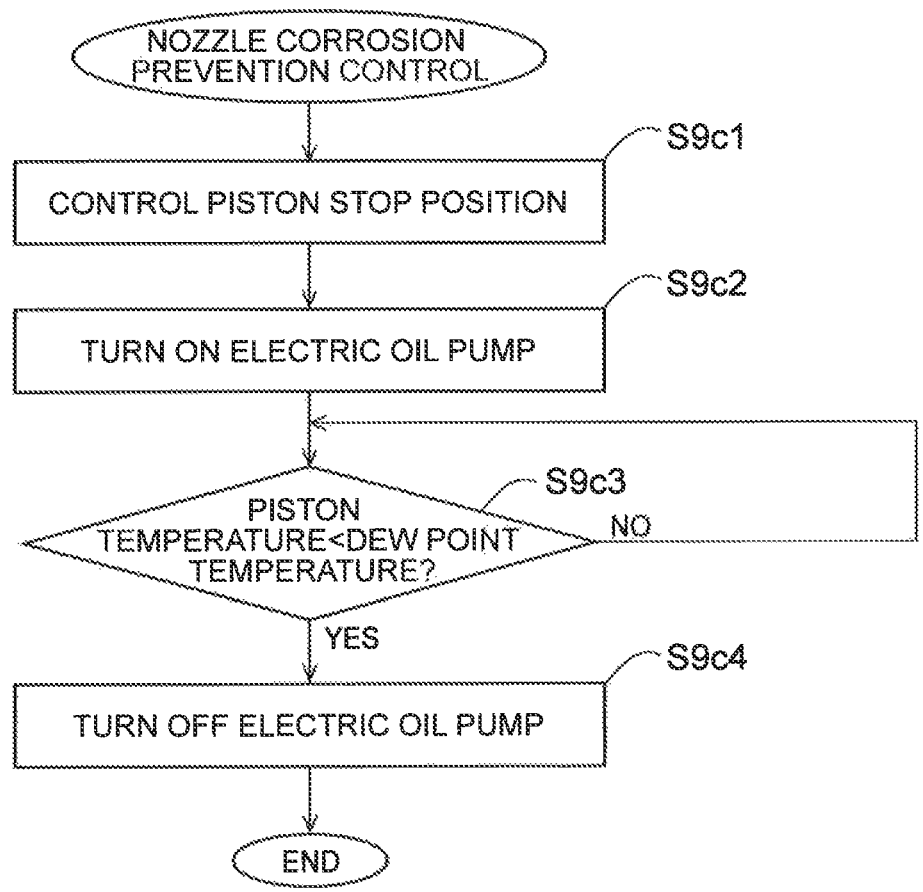
FIG. 11 is a flow diagram illustrating an example of nozzle corrosion prevention control according to the third embodiment.
Figure 12:
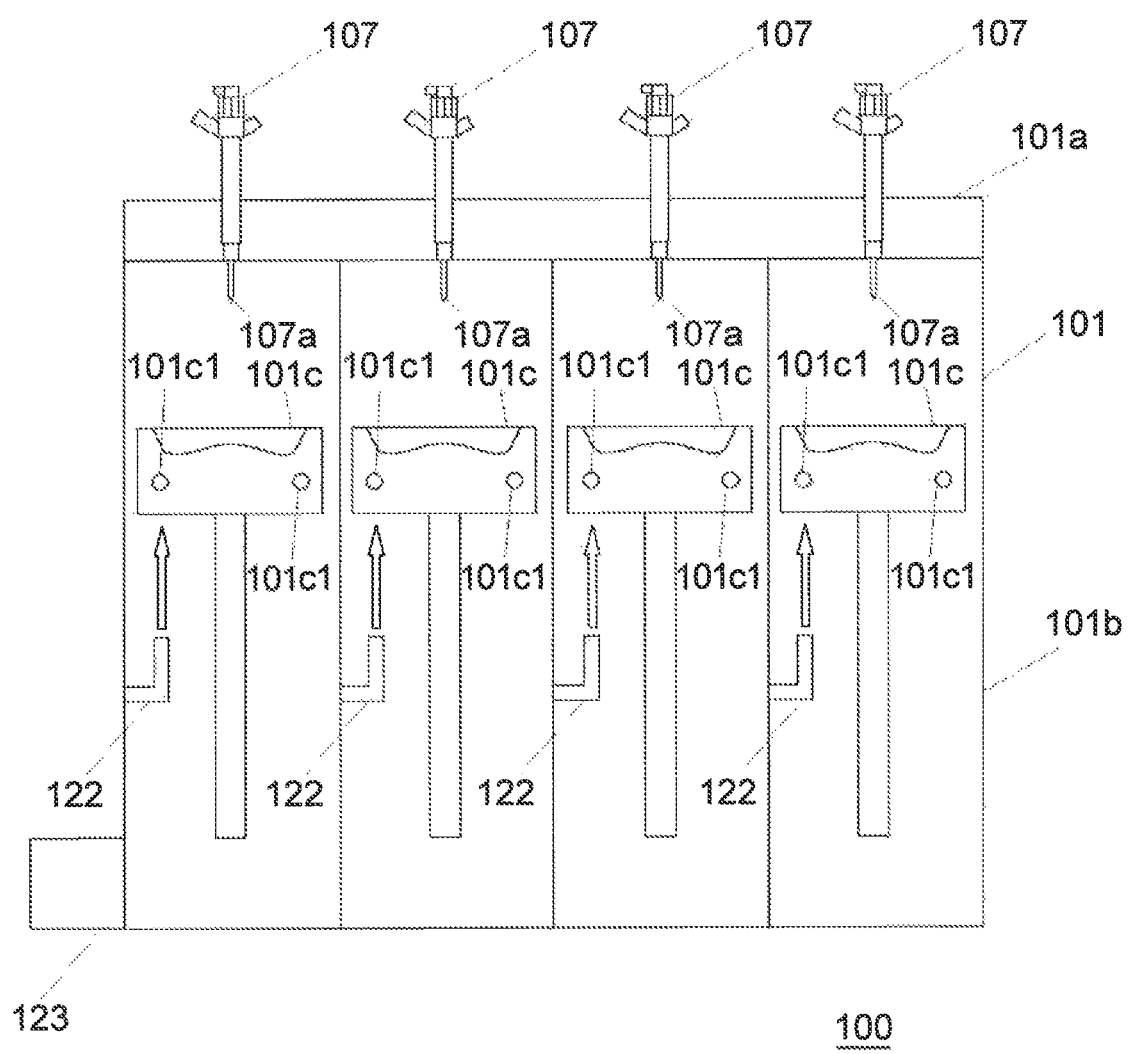
FIG. 12 is an explanatory drawing schematically illustrating the manner of piston cooling according to the third embodiment.
Figure 13A:
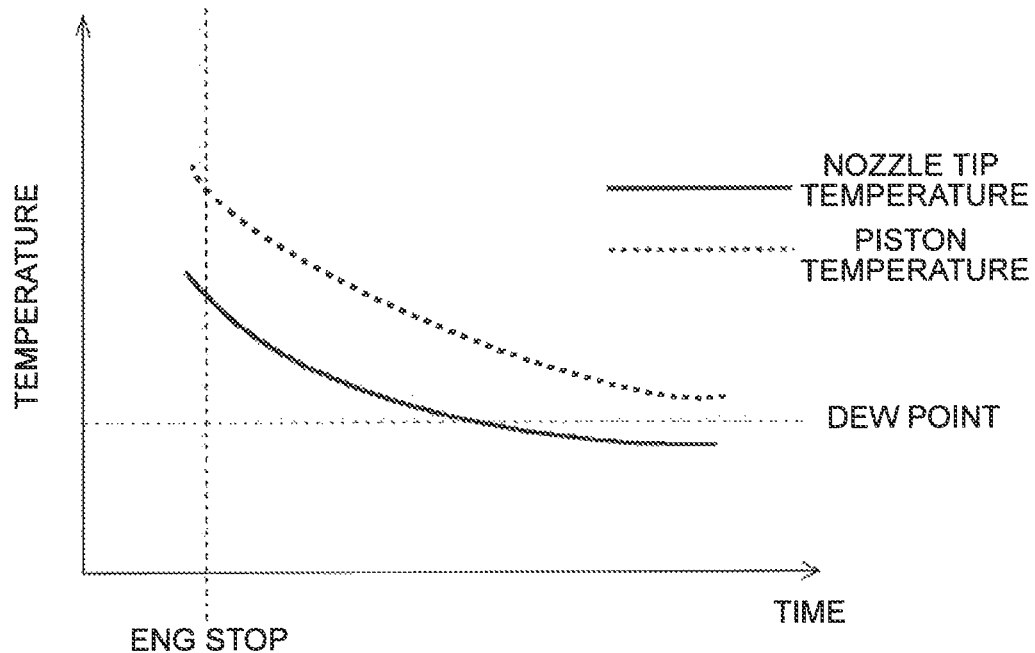
FIGS. 13A and 13B are graphs illustrating the effect of the piston cooling.
Figure 13B:
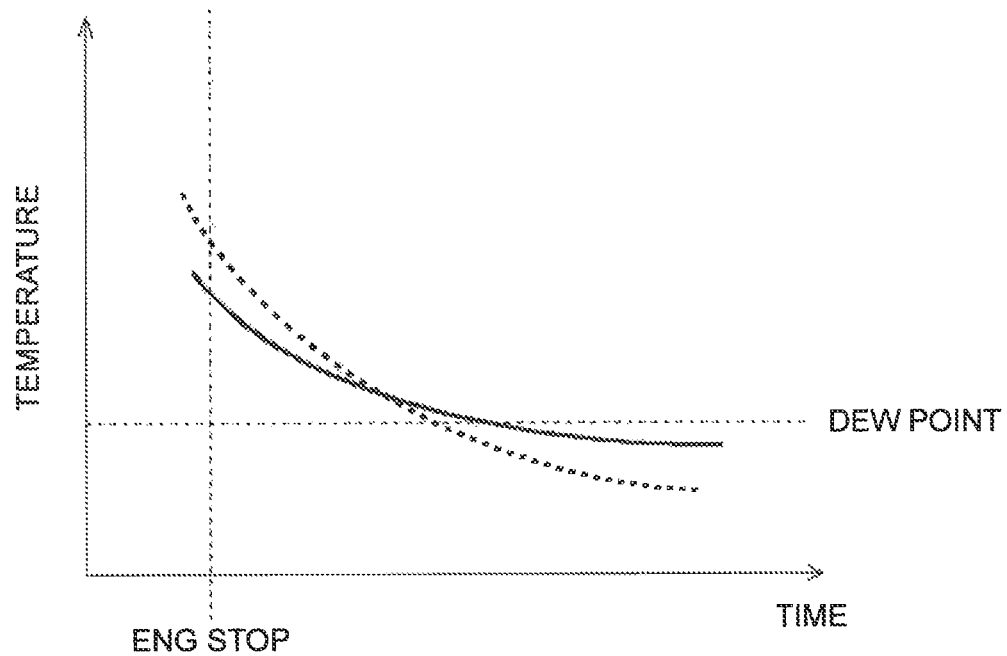

Hereinafter, a third embodiment will be described with reference to FIGS. 10 to 13. FIG. 10 is a block diagram illustrating a main part of the internal combustion engine 100 according to the third embodiment. FIG. 11 is a flow diagram illustrating an example of the control of the internal combustion engine 100 according to the third embodiment. FIG. 12 is an explanatory drawing schematically illustrating the manner of piston cooling according to the third embodiment. FIGS. 13A and 13B are graphs illustrating the effect of the piston cooling.

Referring to FIGS. 10 and 12, the internal combustion engine 100 according to the third embodiment is provided with an electric oil pump 121, which is electrically connected to the ECU 111, as a main part thereof. As illustrated in FIG. 12, the electric oil pump supplies oil to oil jets 122 that cool pistons 101c which are accommodated in a cylinder block 101b. The oil jets 122 are disposed in the respective cylinders, inject the oil toward cooling channels 101c1 of the pistons 101c, and cools the pistons 101c. In addition, the internal combustion engine 100 is provided with a crank position control device 123 that is capable of stopping the piston at a predetermined position. The crank position control device 123 is electrically connected to the ECU 111 and is capable of changing the piston position as desired by rotating a crank with a driving unit which is operated by a command from the ECU 111.

Hereinafter, an example of the nozzle corrosion prevention control (control for the improvement of the temperature reduction rate of a part positioned around the nozzle) that is performed by the third embodiment will be described with reference to the flow diagram illustrated in FIG. 11.

In Step S9c1, a command is issued to the crank position control device 123 and a piston stop position is controlled with reference to a crank angle detected by the crank angle sensor 115. Specifically, the pistons 101c of the four cylinders are stopped at the same position without exception. Accordingly, the oil injection by the oil jets 122 can be uniformly performed on each of the pistons 101c, and the pistons 101c can be uniformly cooled.

In Step S9c2, the electric oil pump 121 is turned ON, the oil is actually injected from the oil jets 122, and the pistons 101e are cooled. The adoption of the electric oil pump 121 is to allow the operation of the oil jets 122 even after the stopping of the internal combustion engine 100.

In Step S9c3, it is determined whether or not the temperature of the piston is lower than a dew point temperature. The piston temperature may be directly measured when the processing of Step S9c3 is performed. In addition, the drive time of the electric oil pump 121 may be managed with the relationship between the drive time of the electric oil pump 121 and piston temperature reduction grasped in advance. In the event of a Yes determination in Step S9c3, the processing proceeds to Step S9c4, the electric oil pump 121 is turned OFF, and the processing is terminated. In the event of a No determination in Step S9c3, the processing of Step S9c3 is repeated.

When the pistons 101c are cooled and the piston temperature reduction rate is improved as described above, the piston temperature is allowed to become equal to or lower than the dew point temperature ahead of the nozzle tip temperature Tnzl. Accordingly, the dew condensation in the nozzle tip portion is avoided. The specific heat of the oil is lower than the specific heat of water and the oil is better in cooling effect than water, and thus the oil is appropriate for the piston cooling.

A state where the piston temperature reaches the dew point ahead of the nozzle tip temperature as illustrated in FIG. 13B can be achieved when the piston cooling is performed in a state where the nozzle tip temperature reaches the dew point ahead of the piston temperature as illustrated in FIG. 13A.

The dew condensation in the nozzle tip portion can be inhibited when the temperature reduction rate of the part positioned around the nozzle 107a of the injector 107 is improved as described above.

The determination of whether or not the dew condensation occurs in the nozzle tip portion according to the third embodiment is identical to that of the first embodiment. In other words, Step S1 to Step S8 in the flow diagram illustrated in FIG. 4 are identical to those of the first embodiment although the determination of whether or not the dew condensation occurs in the nozzle tip portion can be performed by a comparison between the nozzle tip temperature Tnzl and the piston temperature. In other words, it is possible to determine that the dew condensation occurs in the nozzle tip portion when the piston temperature exceeds the nozzle tip temperature Tnzl.

Fourth Embodiment

Figure 14:
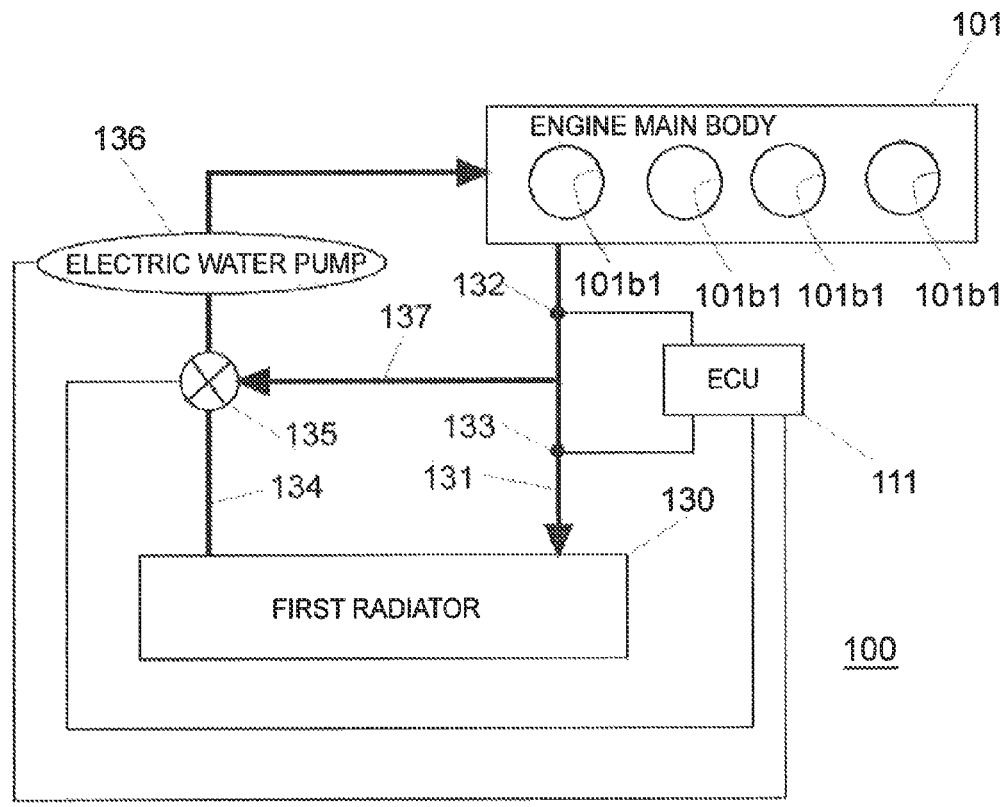
FIG. 14 is an explanatory drawing schematically illustrating a main part of an internal combustion engine according to a fourth embodiment.
Figure 15:
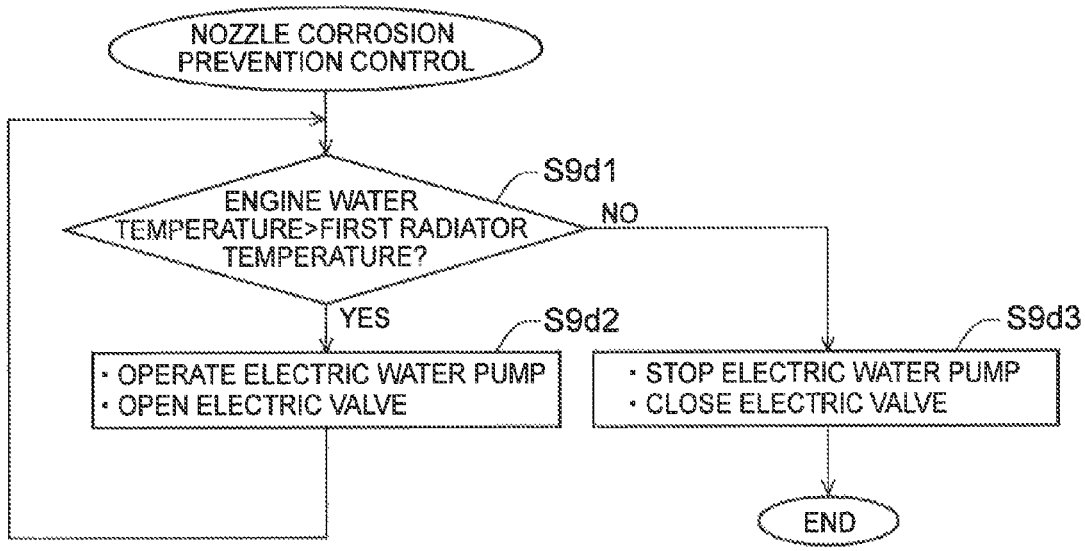
FIG. 15 is a flow diagram illustrating an example of nozzle corrosion prevention control according to the fourth embodiment.
Figure 16A:
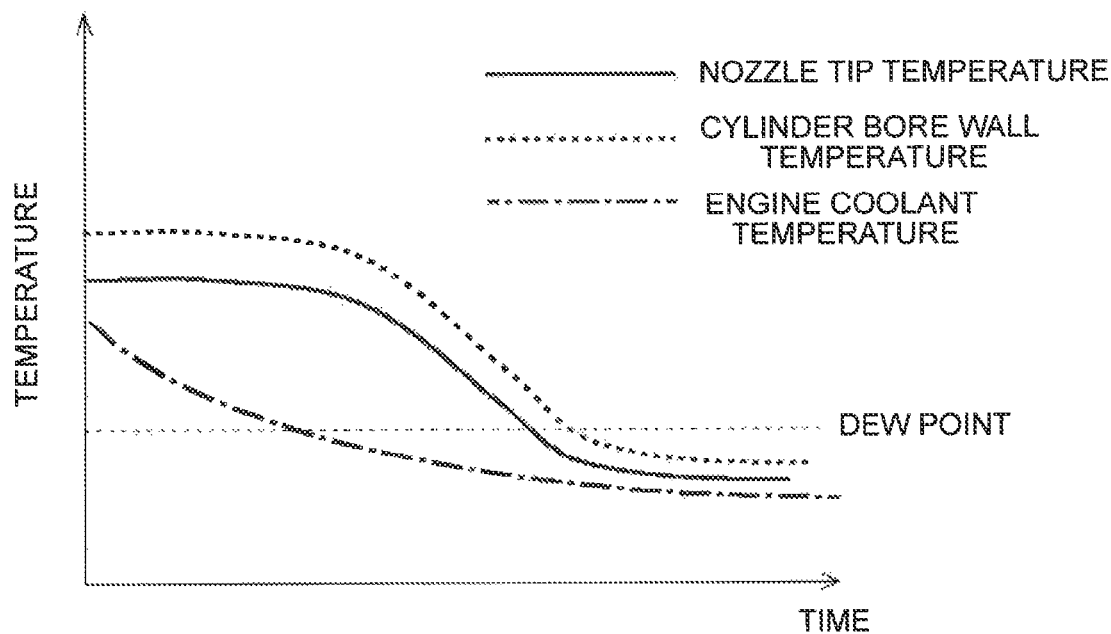
FIGS. 16A and 16B are graphs illustrating the effect of first radiator coolant introduction.
Figure 16B:
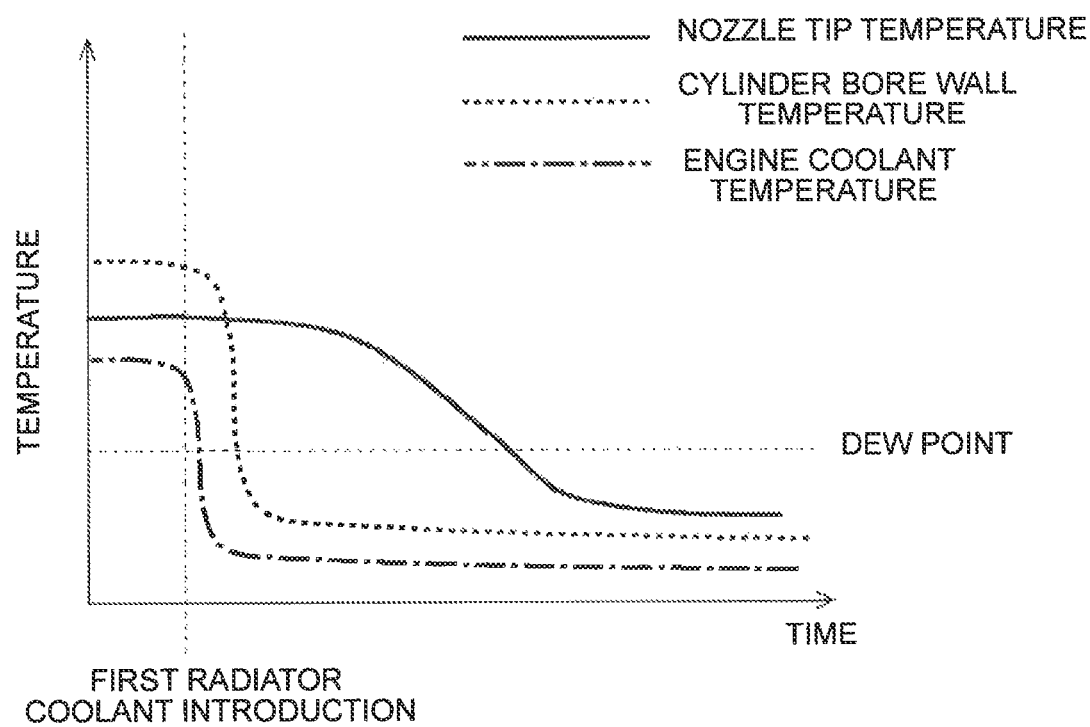

Hereinafter, a fourth embodiment will be described with reference to FIGS. 14 to 16A and 16B. FIG. 14 is an explanatory drawing schematically illustrating a main part of the internal combustion engine 100 according to the fourth embodiment. FIG. 15 is a flow diagram illustrating an example of the control of the internal combustion engine 100 according to the fourth embodiment specifically, coolant introduction control. FIGS. 16A and 16B are graphs illustrating the effect of first radiator coolant introduction.

The internal combustion engine 100 is provided with a first radiator 130 that cools the coolant which flows in the engine main body 101. The first radiator 130 is connected to a water jacket disposed in the engine main body 101 by a first flow path 131. The first flow path 131 allows the coolant to flow from the engine main body 101 side to the first radiator 130 side. A first temperature sensor 132 is mounted on a side of the first flow path 131 close to the engine main body 101. A second temperature sensor 133 is mounted on a side of the first flow path 131 close to the first radiator 130. The first temperature sensor 132 acquires the temperature (engine water temperature) of the coolant flowing in the engine main body 101. The second temperature sensor 133 acquires the temperature (first radiator water temperature) of the coolant in the first radiator. Each of the first temperature sensor 132 and the second temperature sensor 133 is electrically connected to the ECU 111. The first radiator 130 is connected to the engine main body 101 by a second flow path 134. The second flow path 134 allows the coolant to flow from the first radiator 130 side to the engine main body 101 side. An electric valve 135 and an electric water pump 136 are arranged in the second flow path 134. The electric valve 135 and the electric water pump 136 are electrically connected to the ECU 111. A bypass flow path 137 that branches from the first flow path 131 is connected to the electric valve 135.

Hereinafter, an example of the nozzle corrosion prevention control (control for the improvement of the temperature reduction rate of a part positioned around the nozzle) that is performed by the fourth embodiment will be described with reference to the flow diagram illustrated in FIG. 11.

In Step S9d1, it is determined whether or not the engine water temperature acquired by the first temperature sensor 132 is higher than the first radiator water temperature acquired by the second temperature sensor 133. In the event of a Yes determination in Step S9d1, the processing proceeds to Step S9d2, and the electric water pump 136 is operated and the electric valve 135 is allowed to be in an open state. In other words, the coolant in the first radiator 130 having a low temperature is introduced into the engine main body 101. Then, the temperature reduction rate of a cylinder bore wall 101b1 is improved. After the processing of Step S9d2, the processing returns to Step S9d1 and the processing is repeated.

In the event of a No determination in Step S9d1, the processing proceeds to Step S9d3, the electric water pump 136 is stopped and the electric valve 135 is allowed to be in a closed state. The case of a No determination in Step S9d1 is divided into a case where the processing of Step S9d2 has already been performed and a case where the processing of Step S9d2 has yet to be performed. The nozzle corrosion prevention control has already been implemented in a case where the processing of Step S9d2 has already been performed. However, the nozzle corrosion prevention control has yet to be performed in a case where the processing of Step S9d2 has yet to be performed. Herein, an additional measure such as the performing of the injection following the stopping of the engine may be adopted. The processing is terminated (ends) after Step S9d3.

When the cylinder bore wall 101b1 is cooled and the cylinder bore wall temperature reduction rate is improved as described above, the cylinder bore wall temperature is allowed to become equal to or lower than the dew point temperature ahead of the nozzle tip temperature Tnzl. Accordingly, the dew condensation in the nozzle tip portion is avoided.

A state where the cylinder bore wall temperature reaches the dew point ahead of the nozzle tip temperature as illustrated in FIG. 16B can be achieved when the cooling of the cylinder bore wall is performed in a state where the nozzle tip temperature reaches the dew point ahead of the cylinder bore wall temperature as illustrated in FIG. 16A.

The dew condensation in the nozzle tip portion can be inhibited when the temperature reduction rate of the part positioned around the nozzle 107a of the injector 107 is improved as described above.

The determination of whether or not the dew condensation occurs in the nozzle tip portion according to the fourth embodiment is identical to that of the first embodiment. In other words, Step S1 to Step S8 in the flow diagram illustrated in FIG. 4 are identical to those of the first embodiment although the determination of whether or not the dew condensation occurs in the nozzle tip portion can be performed by a comparison between the nozzle tip temperature Tnzl and the cylinder bore wall temperature obtained when the engine is stopped. For example, it is possible to determine that the dew condensation occurs in the nozzle tip portion when the nozzle tip temperature Tnzl is lower than the cylinder bore wall temperature+α° C.

Fifth Embodiment

Figure 17:
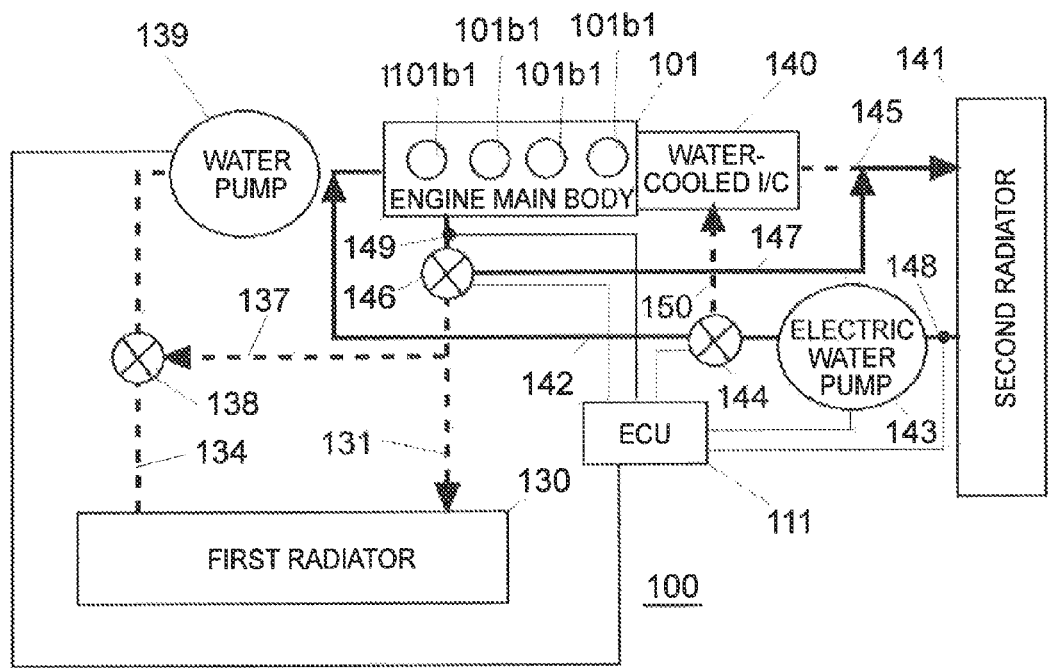
FIG. 17 is an explanatory drawing schematically illustrating a main part of an internal combustion engine according to a fifth embodiment.
Figure 18:
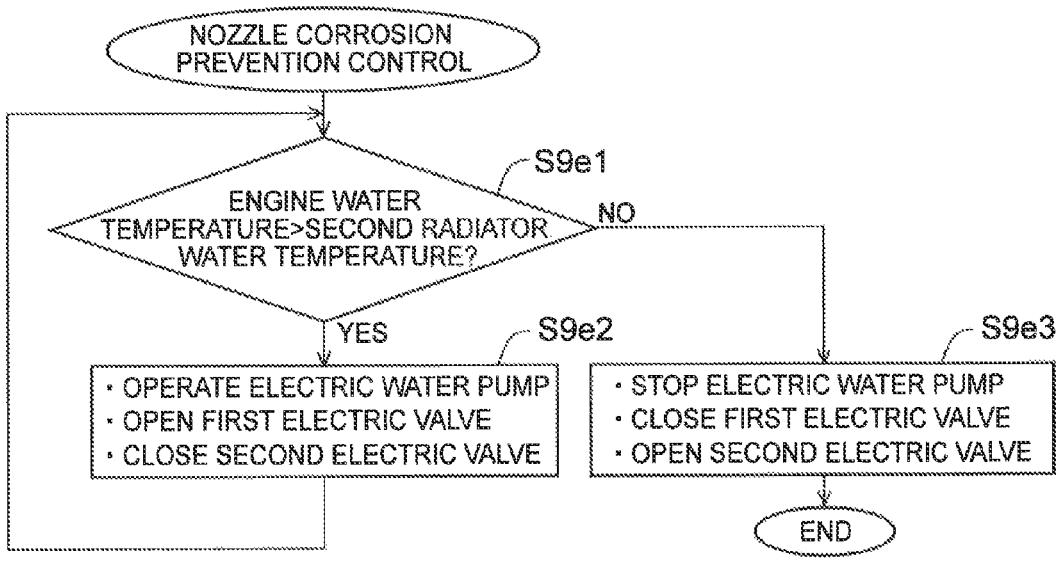
FIG. 18 is a flow diagram illustrating an example of nozzle corrosion prevention control according to the fifth embodiment.

Hereinafter, a fifth embodiment will be described with reference to FIGS. 17 and 18. FIG. 17 is an explanatory drawing schematically illustrating a main part of the internal combustion engine 100 according to the fifth embodiment. FIG. 18 is a flow diagram illustrating an example of the control of the internal combustion engine 100 according to the fifth embodiment, specifically, coolant introduction control.

The internal combustion engine 100 is provided with the first radiator 130 and the first flow path 131 described in the fourth embodiment, is also provided with the second flow path 134, is further provided with a temperature-sensitive thermostat 138 instead of the electric valve 135 of the fourth embodiment, and is further provided with a mechanical water pump 139 instead of the electric water pump 136.

In addition, the internal combustion engine 100 is provided with a second radiator 141 that cools a coolant which is introduced into a water-cooled intercooler (I/C) 140. The second radiator 141 is connected to the water jacket disposed in the engine main body 101 by a third flow path 142. The third flow path 142 allows the coolant to flow from second radiator 141 side to the engine main body 101 side. An electric water pump 143 and a first electric valve 144 are arranged in the third flow path 142. The second radiator 141 is connected to the water-cooled intercooler 140 by a fourth flow path 145. The fourth flow path 145 allows the coolant to flow from the water-cooled intercooler 140 side to the second radiator side. The fourth flow path 145 is connected to the engine main body 101 by a fifth flow path 147. The fifth flow path 147 allows the coolant to flow from the engine main body 101 side to the fourth flow path 145 side. A second electric valve 146 is arranged in the fifth flow path 147. A first temperature sensor 148 is mounted on the third flow path 142 between the second radiator 141 and the electric water pump 143. A second temperature sensor 149 is mounted on the fifth flow path 147 between the engine main body 101 and the second electric valve 146. The first electric valve 144 is connected to the water-cooled intercooler 140 by a sixth flow path 150. Each of the electric water pump 143, the first electric valve 144, the second electric valve 146, the first temperature sensor 148, and the second temperature sensor 149 is electrically connected to the ECU 111. The first temperature sensor 148 acquires the temperature (second radiator water temperature) of the coolant in the second radiator. The second temperature sensor 149 acquires the temperature (engine water temperature) of the coolant flowing in the engine main body 101.

Hereinafter, an example of the nozzle corrosion prevention control (control for the improvement of the temperature reduction rate of a part positioned around the nozzle) that is performed by the fifth embodiment will be described with reference to the low diagram illustrated in FIG. 18.

In Step S9e1, it is determined whether or not the engine water temperature acquired by the second temperature sensor 149 is higher than the second radiator water temperature acquired by the first temperature sensor 148. In the event of a Yes determination in Step S9e1, the processing proceeds to Step S9e2, the electric water pump 143 is operated, the first electric valve 135 is allowed to be in an open state, and the second electric valve 146 is allowed to be in a closed state. In other words, the coolant in the second radiator 141 having a low temperature is introduced into the engine main body 101. Then, the temperature reduction rate of the cylinder bore wall 101b1 is improved. After the processing of Step S9e2, the processing returns to Step S9e1 and the processing is repeated.

In the event of a No determination in Step S9e1, the processing proceeds to Step S9e3, the electric water pump 143 is stopped, the first electric valve 135 is allowed to be in a closed state, and the second electric valve 146 is allowed to be in an open state. The case of a No determination in Step S9e1 is divided into a case where the processing of Step S9e2 has already been performed and a case where the processing of Step S9e2 has yet to be performed. The nozzle corrosion prevention control has already been implemented in a case where the processing of Step S9e2 has already been performed. However, the nozzle corrosion prevention control has yet to be performed in a case where the processing of Step S9e2 has yet to be performed. Herein, an additional measure such as the performing of the injection following the stopping of the engine may be adopted. The processing is terminated (ends) after Step S9d3.

When the cylinder bore wall 101b1 is cooled and the cylinder bore wall temperature reduction rate is improved as described above, the cylinder bore wall temperature is allowed to become equal to or lower than the dew point temperature ahead of the nozzle tip temperature Tnzl. Accordingly, the dew condensation in the nozzle tip portion is avoided.

In the fifth embodiment, the coolant in the second radiator 141, in which a coolant flows with a lower temperature than in the first radiator 130, is introduced into the engine main body 101. Accordingly, the cylinder bore wall temperature is more likely to be reduced than in the fourth embodiment.

Sixth Embodiment

Figure 19:
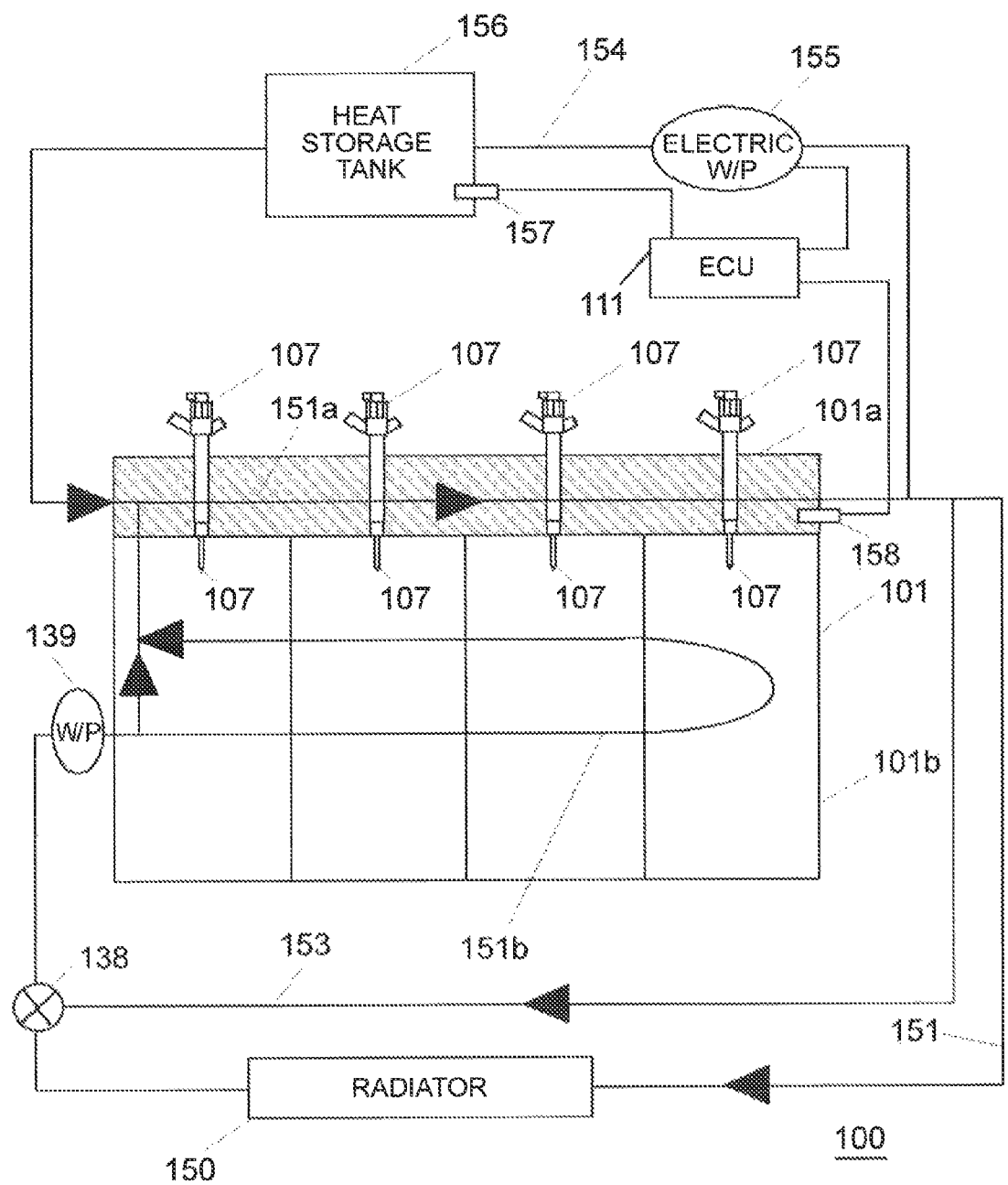
FIG. 19 is an explanatory drawing schematically illustrating a main part of an internal combustion engine according to a sixth embodiment.
Figure 20:
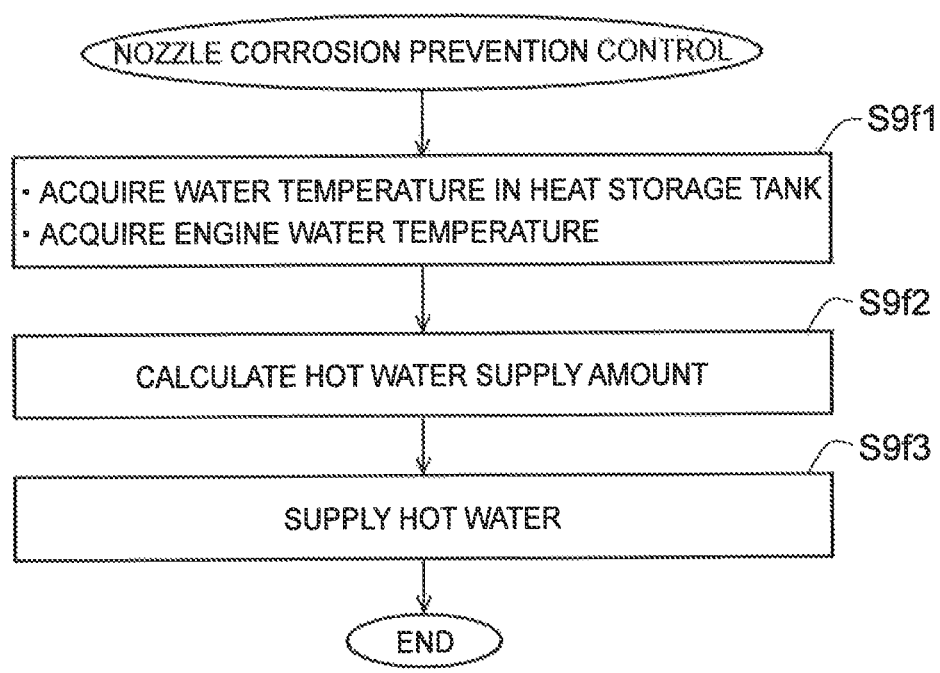
FIG. 20 is a flow diagram illustrating an example of nozzle corrosion prevention control according to the sixth embodiment.
Figure 21:
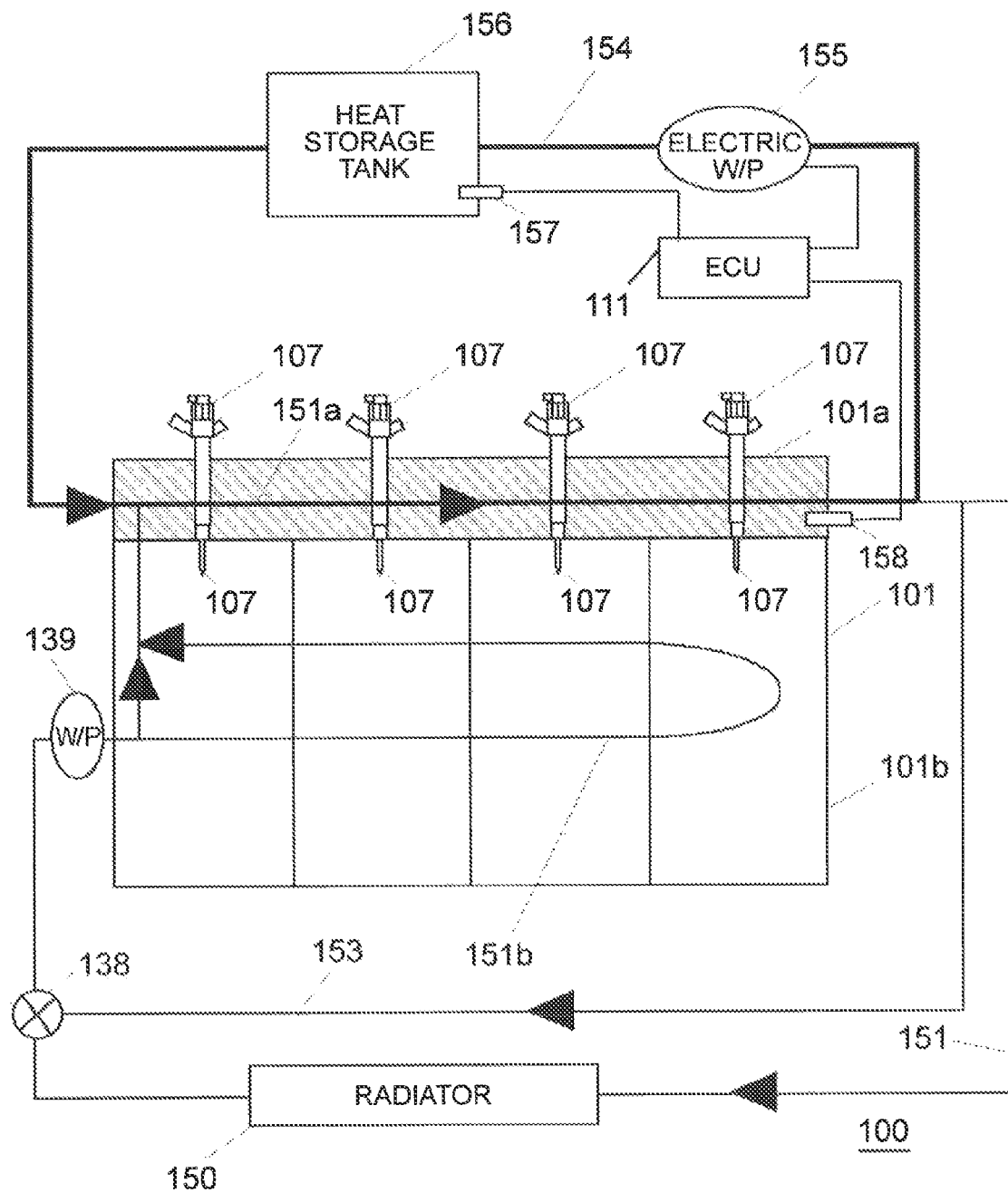
FIG. 21 is an explanatory drawing illustrating how hot water is supplied to a cylinder head of the internal combustion engine according to the sixth embodiment.

Hereinafter, a sixth embodiment will be described with reference to FIGS. 19 to 21. FIG. 19 is an explanatory drawing schematically illustrating a main part of the internal combustion engine 100 according to the sixth embodiment. FIG. 20 is a flow diagram illustrating an example of the control of the internal combustion engine 100 according to the sixth embodiment, specifically, hot water flow control. FIG. 21 is an explanatory drawing illustrating how hot water is supplied to the cylinder head 101a of the internal combustion engine 100 according to the sixth embodiment.

The internal combustion engine 100 is provided with a flow path 151 for the flow of a coolant that circulates in the water jacket disposed therein. The coolant circulation flow path 151 includes an in-head flow path 151a for flow in the cylinder head 101a and an in-block flow path 101b for flow in the cylinder block 101b. A radiator 150, a thermostat valve 152 and the water pump 139 are arranged in the coolant circulation flow path 151. A bypass flow path 153 that bypasses the radiator 150 is connected to the thermostat valve 152. The internal combustion engine 100 is provided with a hot water circulation flow path 154. The hot water circulation flow path 154 serves also as the in-head flow path 151a. An electric water pump 155 and a heat storage tank 156 are arranged in the hot water circulation flow path 154. A first temperature sensor 157 is mounted on the heat storage tank 156. The first temperature sensor 157 acquires the temperature of the hot water in the heat storage tank 156. A second temperature sensor 158 is mounted on the cylinder head 101a. Each of the second temperature sensor 158, the first temperature sensor 157, and the electric water pump 155 is electrically connected to the ECU 111.

Hereinafter, an example of the nozzle corrosion prevention control (control for nozzle heat dissipation rate reduction) that is performed by the sixth embodiment will be described with reference to the flow diagram illustrated in FIG. 20.

In Step S9/1, the engine water temperature and the temperature of the hot water in the heat storage tank 156 are acquired. The state in the cylinder of the engine main body 101 is grasped from the engine water temperature acquired by the second temperature sensor 158.

Then, in Step S9/2, a heat amount that should be applied to the injector 107 so as to avoid the dew condensation in the nozzle tip portion is calculated from the state in the cylinder of the engine main body. Then, a hot water supply amount appropriate for the heat amount is calculated. In Step S9/3, the electric water pump 155 is operated for the period of time corresponding to the calculated hot water supply amount.

Then, the heat amount of the cylinder head 101a is increased and the nozzle tip temperature rises. As a result, the reduction rate of the nozzle tip temperature Tnzl can be reduced. Then, the temperatures of locations other than the nozzle tip portion, for example, the cylinder bore wall and the piston, are relatively reduced, and the cylinder bore wall temperature and the piston temperature become equal to or lower than the dew point temperature ahead of the nozzle tip temperature Tnzl. Accordingly, the dew condensation in the nozzle tip portion is avoided.

The above-described embodiments are mere examples for the implementation of the invention and the invention is not limited thereto. Various modifications of the embodiments are also included in the invention, and it should be apparent from the above description that a variety of other embodiments are also possible within the scope of the invention.

REFERENCE SIGNS LIST

1 FUEL INJECTION DEVICE
100 INTERNAL COMBUSTION ENGINE
101 ENGINE MAIN BODY
102 INTAKE MANIFOLD
103 EXHAUST MANIFOLD
104 INTAKE PIPE
105 EXHAUST PIPE
107 INJECTOR
111 ECU
122 OIL JET
130 FIRST RADIATOR
141 SECOND RADIATOR
156 HEAT STORAGE TANK

The invention claimed is:

1. A method of operating an internal combustion engine, the method comprising:
   determining, via one or more sensors, a rotation speed, an injection timing, an injection amount, a water temperature, and a fuel temperature of the internal combustion engine;
   determining a nozzle heat receiving amount of an injector and a nozzle tip temperature of the injector, based on the rotation speed, the injection timing, the injection amount, the water temperature, and the fuel temperature of the internal combustion engine, at a point in time when ignition is turned off; and
   determining the occurrence or non-occurrence of dew condensation in a tip portion of a nozzle based on the nozzle heat receiving amount and the nozzle tip temperature of the injector at the point in time when ignition is turned off.

2. The method according to claim 1, further comprising performing at least one of control for reducing nozzle heat dissipation rate or control for increasing temperature reduction rate of a part positioned around the nozzle when the dew condensation occurs in the nozzle tip portion.

3. The method according to claim 2, further comprising performing racing implementation control during the control for reducing the nozzle heat dissipation rate.

4. The method according to claim 2, further comprising performing idle extension control during the control for reducing the nozzle heat dissipation rate.

5. The method according to claim 4, further comprising raising an idle rotation speed during the idle extension control.

6. The method according claim 2, further comprising increasing a piston temperature reduction rate during the control for increasing the temperature reduction rate of the part positioned around the nozzle.

7. The method according to claim 2, further comprising allowing a coolant in a radiator to be introduced into an engine main body and increasing temperature reduction rate of a cylinder bore wall during the control for increasing the temperature reduction rate of the part positioned around the nozzle.

8. The method according to claim 2, further comprising reducing a nozzle tip temperature reduction rate by supplying hot water in a heat storage tank to a cylinder head on which the injector is mounted during the control for reducing the nozzle heat dissipation rate.

9. The method according to claim 1, further comprising calculating a nozzle tip temperature reduction rate based on the nozzle heat receiving amount and calculating a dew point arrival time based on the nozzle tip temperature reduction rate, and
   determining the occurrence or non-occurrence of the dew condensation in the nozzle tip portion based on the dew point arrival time.

* * * * *